United States Patent
Lee et al.

(10) Patent No.: US 9,284,582 B2
(45) Date of Patent: Mar. 15, 2016

(54) **METHOD FOR PREPARING MUTANT *ESCHERICHIA COLI* CAPABLE OF SIMULTANEOUSLY UTILIZING GLUCOSE AND XYLOSE**

(71) Applicant: UNIST ACADEMY-INDUSTRY RESEARCH CORPORATION, Ulsan (KR)

(72) Inventors: Sung Kuk Lee, Ulsan (KR); Goo Hee Kim, Ulsan (KR); Seong Hun Jeong, Ulsan (KR); Suk Min Kim, Pohang-si (KR); Bae Young Choi, Seoul (KR)

(73) Assignee: UNIST Academy-Industry Research Corporation, Ulsan (KR)

( * ) Notice: Subject to any disclaimer, the term of this patent is extended or adjusted under 35 U.S.C. 154(b) by 0 days.

(21) Appl. No.: 14/322,007

(22) Filed: Jul. 2, 2014

(65) Prior Publication Data

US 2015/0050691 A1 Feb. 19, 2015

(51) Int. Cl.
*C12P 7/18* (2006.01)
*C12N 1/22* (2006.01)
*C12P 7/10* (2006.01)

(52) U.S. Cl.
CPC ... *C12P 7/18* (2013.01); *C12N 1/22* (2013.01); *C12P 7/10* (2013.01); *C12P 2203/00* (2013.01)

(58) Field of Classification Search
None
See application file for complete search history.

*Primary Examiner* — Anne Gussow
*Assistant Examiner* — Mindy G Brown
(74) *Attorney, Agent, or Firm* — Sughrue Mion, PLLC

(57) ABSTRACT

The present invention relates to a method for preparing a mutant *E. coli* strain, capable of simultaneously using glucose and xylose, by genetic engineering and evolutionary adaptation; the mutant *E. coli* prepared using the same; and a method for producing biofuels, biologically active ingredients, medicinal materials or base chemicals for the chemical industry using the mutant *E. coli*. Being capable of simultaneously using glucose and xylose, in contrast to wild-type *E. coli*, the mutant *E. coli* can be effectively applied to the enzymatic saccharification process of producing biofuels from a biomass.

13 Claims, 28 Drawing Sheets

FIG. 10

(1) pyrE upstream region

```
MG1655   TCATCTTACTTTTCTACAGACAAAAAAAAGCGACTCATCAGTCGCCTTAAAAATCAGTT  (SEQ ID NO: 61)
AXcp     TCATCTTACTTTTCTACAGACAAAAAAAAGCGACTCATCAGTCGCCTTAAAAATCAGTT  (SEQ ID NO: 62)
AXcpX39  TCATCTTACTTTTCTACAGACAAAAAAAAGCGACTCATCAGTCGCCTTAAAAATCAGTT  (SEQ ID NO: 63)
AXcpAX39 TCATCTTACTTTTCTACAGACAAAAAAAAGCGACTCATCAGTCGCCTTAAAAATCAGTT  (SEQ ID NO: 64)
Region   42 base upstream from start codon
```

(2) ybjG coding region

```
MG1655   TTC CTG CAT CAT GCG GCG GAT GAC TCA TTC CCA AGC GAT CAC GGT  (SEQ ID NO: 65)
AXcp     TTC CTG CAT CAT GCG GCG GAT GAC TCA TTC CCA AGC GAT CAC GGT  (SEQ ID NO: 66)
AXcpX39  TTC CTG CAT CAT GCG GCG GAT GAC TCA TTC CCA AGC GAT CAC GGT  (SEQ ID NO: 67)
AXcpAX39 TTC CTG CAT CAT GCG GCG GAT GAC TCA TTC CCA AGC GAT CAC GGT  (SEQ ID NO: 68)
Codon    92  93  94  95  96  97  98  99  100 101 102 103 104 105 106
```

(3) araE coding region

```
MG1655   TTC CGC CTG GGG CGT AAA TAC AGC CTG ATG GCG GGG GCC ATC CTG  (SEQ ID NO: 69)
AXcp     TTC CGC CTG GGG CGT AAA TAC AGC CTG ATG GCG GGG GCC ATC CTG  (SEQ ID NO: 70)
AXcpX39  TTC CGC CTG GGG CGT AAA TAC AGC CTG ATG GCG GGG GCC ATC CTG  (SEQ ID NO: 71)
AXcpAX39 TTC CGC CTG GGG CGT AAA TAC AGC CTG ATG GCG GGG GCC ATC CTG  (SEQ ID NO: 72)
Codon    84  85  86  87  88  89  90  91  92  93  94  95  96  97  98
```

(4) xkiC upstream region

```
MG1655   ATCAGGTTCCGCGGATCCCGAATAAACGGTTCAGCCAGTTAAGGCACTCCGACAAGAAA  (SEQ ID NO: 73)
AXcp     ATCAGGTTCCGCGGATCCCGAATAAACGGTTCAGCCAGTTAAGGCACTCCGACAAGAAA  (SEQ ID NO: 74)
AXcpX39  ATCAGGTTCCGCGGATCCCGAATAAACGGTTCAGCCAGTTAAGGCACTCCGACAAGAAA  (SEQ ID NO: 75)
AXcpAX39 ATCAGGTTCCGCGGATCCCGAATAAACGGTTCAGCCAGTTAAGGCACTCCGACAAGAAA  (SEQ ID NO: 76)
Region   150 base upstream from start codon
```

(5) araF coding region

```
MG1655   GCC CTG GCA GCC ATT GGT CTG GCA GCC GTT ATG TCA CAA TCC GCT  (SEQ ID NO: 77)
AXcp     GCC CTG GCA GCC ATT GGT CTG GCA GCC GTT ATG TCA CAA TCC GCT  (SEQ ID NO: 78)
AXcpX39  GCC CTG GCA GCC                         GTT ATG TCA CAA TCC GCT  (SEQ ID NO: 79)
AXcpAX39 GCC CTG GCA GCC                         GTT ATG TCA CAA TCC GCT  (SEQ ID NO: 80)
Codon    7   8   9   10  11  12  13  14  15  16  17  18  19  20  21
```

(6) xylAB CP25 promoter region

```
Reference CTTTGGCAGTTATTCTTGACATGTAGTGAGGGGCTGGTATAATCGATAGTACTGTTCACACAGGAA  (SEQ ID NO: 81)
AXcp      CTTTGGCAGTTATTCTTGACATGTAGTGAGGGGCTGGTATAATCGATAGTACTGTTCACACAGGAA  (SEQ ID NO: 82)
AXcpX39   CTTTGGCAGTTATTCTTGACATGTAGTGAGGGGCTGGTATAATCGATAGTACTGTTCACACAGGAA  (SEQ ID NO: 83)
AXcpAX39  CTTTGGCAGTTATTCTTGACATGTAGTGAGGGGCTGGTATAATCGATAGTACTGTTCACACAGGAA  (SEQ ID NO: 84)
Region         -35 region                    -10 region
```

FIG. 11

(A) AraE

| | | | |
|---|---|---|---|
| MG1655 | LDIGVIAGALPETTDHEVLTSRLQEWVVSSMMLGAAIGALFNGWLSFLGEKVSLMAGAI | 132 | (SEQ ID NO: 85) |
| AXqpX50 | LDIGVIAGALPETTDHEVLTSRLQEWVVSSMMLGAAIGALFNGWLSFLGE------A | 126 | (SEQ ID NO: 86) |

(B) AraF

| | | | |
|---|---|---|---|
| MG1655 | MHKFTKALAALAIGLAAVMSQSAMAENLKLGFLVKQPEEPWFQTEWKFADKAGKDLGFEVIK | 60 | (SEQ ID NO: 87) |
| AXqpX50 | MHKFTKALAA-------VMSQSAMAENLKLGFLVKQPEEPWFQTEWKFADKAGKDLGFEVIK | 55 | (SEQ ID NO: 88) |

(C) AraE

| | | | |
|---|---|---|---|
| MG1655 | LGRKYILMAGAILFVLGSIGSAFATSVEMLIAARVVLGTAVGIASYTAPLYLSEMASENV | 180 | (SEQ ID NO: 89) |
| AXqpX50 | LGRKYILMAGAILFVLGSIGSAFATSVEMLIAARVVLGTAVGIASYTAPLYLSEMASENV | 180 | (SEQ ID NO: 90) |

(D) YujG

| | | | |
|---|---|---|---|
| MG1655 | AIALAVSLFVSWTMGHLFPHDRPFVENIGYNFLHHAADSFESDHGTVIETFALAFLCWH | 120 | (SEQ ID NO: 91) |
| AXqpX50 | AIALAVSLFVSWTMGHLFPHDRPFVENIGYNFLHHAADSFESDHGTVIETFALAFLCWH | 120 | (SEQ ID NO: 92) |

```
                              SEQUENCE LISTING

<160> NUMBER OF SEQ ID NOS: 92

<210> SEQ ID NO 1
<211> LENGTH: 73
<212> TYPE: DNA
<213> ORGANISM: Escherichia coli

<400> SEQUENCE: 1
cggatcctac ctgacgcttt ttatcgcaac tctctactgt ttctccatac ccgttttttt      60
ggatggagtg aaa                                                         73

<210> SEQ ID NO 2
<211> LENGTH: 85
<212> TYPE: DNA
<213> ORGANISM: Escherichia coli

<400> SEQUENCE: 2
aattctgcga tgtgatattg ctctcctatg gagaattaat ttctcgctaa aactatgtca      60
acacagtcac ttatctttta gttaa                                            85

<210> SEQ ID NO 3
<211> LENGTH: 85
<212> TYPE: DNA
<213> ORGANISM: Escherichia coli

<400> SEQUENCE: 3
catatttatg ctgtttccga cctgacacct gcgtgagttg ttcacgtatt ttttcactat      60
gtcttactct ctgctggcag gaaaa                                            85

<210> SEQ ID NO 4
<211> LENGTH: 85
<212> TYPE: DNA
<213> ORGANISM: Escherichia coli

<400> SEQUENCE: 4
ggtaatgccg cgggtgatgg atgatgtcgt aatattgggc actcccttttc agttgctcaa     60 ttatgttatt tcacactgct attga                                            85

<210> SEQ ID NO 5
<211> LENGTH: 85
<212> TYPE: DNA
<213> ORGANISM: Escherichia coli

<400> SEQUENCE: 5
cgtaatcgaa agataaaaat ctgtaattgt tttcccctgt ttagttgcta aaaattggtt      60
acgtttatcg cggtgattgt tactt                                            85

<210> SEQ ID NO 6
<211> LENGTH: 75
<212> TYPE: DNA
<213> ORGANISM: Artificial Sequence
<220> FEATURE:
<223> OTHER INFORMATION: CP25 promoter

<400> SEQUENCE: 6
```

-continued

```
ctttggcagt ttattcttga catgtagtga gggggctggt ataatcacat agtactgttc    60
acacaggaaa cagct                                                    75

<210> SEQ ID NO 7
<211> LENGTH: 76
<212> TYPE: DNA
<213> ORGANISM: Artificial Sequence
<220> FEATURE:
<223> OTHER INFORMATION: CP6 promoter

<400> SEQUENCE: 7
catgtgggag tttattcttg acacagatat ttccggatga tataataact gagtactgtt    60
cacacaggaa acagct                                                   76

<210> SEQ ID NO 8
<211> LENGTH: 67
<212> TYPE: DNA
<213> ORGANISM: Artificial Sequence
<220> FEATURE:
<223> OTHER INFORMATION: SOEing primer

<400> SEQUENCE: 8
ccctatgcta ctccgtcaag ccgtcaattg tctgattcgt taccaagtgt aggctggagc    60
tgcttcg                                                             67

<210> SEQ ID NO 9
<211> LENGTH: 98
<212> TYPE: DNA
<213> ORGANISM: Artificial Sequence
<220> FEATURE:
<223> OTHER INFORMATION: SOEing primer

<400> SEQUENCE: 9
catagctgtt tcctgtgtga acagtactat gtgattatac cagcccctc actacatgtc     60 aagaataaac tgccaaagat tccggggatc cgtcgacc                            98

<210> SEQ ID NO 10
<211> LENGTH: 74
<212> TYPE: DNA
<213> ORGANISM: Artificial Sequence
<220> FEATURE:
<223> OTHER INFORMATION: SOEing primer

<400> SEQUENCE: 10
cccgcaaaga acgtggcgtt aaagcagatt ccgtattgat agtaaccata gctgtttcct    60
gtgtgaacag tact                                                     74

<210> SEQ ID NO 11
<211> LENGTH: 20
<212> TYPE: DNA
<213> ORGANISM: Artificial Sequence
<220> FEATURE:
<223> OTHER INFORMATION: Sequencing primer

<400> SEQUENCE: 11
aactggttat tcggggcatc                                               20

<210> SEQ ID NO 12
<211> LENGTH: 20
<212> TYPE: DNA
<213> ORGANISM: Artificial Sequence
<220> FEATURE:
```

<223> OTHER INFORMATION: Sequencing primer

<400> SEQUENCE: 12
aggcgtgcca gaaacttaac                                                  20

<210> SEQ ID NO 13
<211> LENGTH: 70
<212> TYPE: DNA
<213> ORGANISM: Artificial Sequence
<220> FEATURE:
<223> OTHER INFORMATION: SOEing primer

<400> SEQUENCE: 13
ggtaatgcgg cctattgact ggttaaaaag aagacatccc gcatgggtag tgtaggctgg      60
agctgcttcg                                                             70

<210> SEQ ID NO 14
<211> LENGTH: 99
<212> TYPE: DNA
<213> ORGANISM: Artificial Sequence
<220> FEATURE:
<223> OTHER INFORMATION: SOEing primer

<400> SEQUENCE: 14
catagctgtt tcctgtgtga acagtactca gttattatat catccggaaa tatctgtgtc      60
aagaataaac tcccacatga ttccggggat ccgtcgacc                             99

<210> SEQ ID NO 15
<211> LENGTH: 78
<212> TYPE: DNA
<213> ORGANISM: Artificial Sequence
<220> FEATURE:
<223> OTHER INFORMATION: SOEing primer

<400> SEQUENCE: 15
gacataacgg ctgccagacc aatggctgcc agggctttag taaatttgtg catagctgtt      60
tcctgtgtga acagtact                                                    78

<210> SEQ ID NO 16
<211> LENGTH: 21
<212> TYPE: DNA
<213> ORGANISM: Artificial Sequence
<220> FEATURE:
<223> OTHER INFORMATION: Sequencing primer

<400> SEQUENCE: 16
gctctcatta tacgtgttct g                                                21

<210> SEQ ID NO 17
<211> LENGTH: 21
<212> TYPE: DNA
<213> ORGANISM: Artificial Sequence
<220> FEATURE:
<223> OTHER INFORMATION: Sequencing primer

<400> SEQUENCE: 17
cctcaaaccc taaatccttc c                                                21

<210> SEQ ID NO 18
<211> LENGTH: 68
<212> TYPE: DNA
<213> ORGANISM: Artificial Sequence
<220> FEATURE:
<223> OTHER INFORMATION: SOEing primer

```
<400> SEQUENCE: 18
tatctgctgt aaaattaggt ggttaataat aatctcaata attcaacgtg taggctggag      60
ctgcttcg                                                               68

<210> SEQ ID NO 19
<211> LENGTH: 99
<212> TYPE: DNA
<213> ORGANISM: Artificial Sequence
<220> FEATURE:
<223> OTHER INFORMATION: SOEing primer

<400> SEQUENCE: 19
catagctgtt tcctgtgtga acagtactca gttattatat catccggaaa tatctgtgtc      60
aagaataaac tcccacatga ttccggggat ccgtcgacc                             99

<210> SEQ ID NO 20
<211> LENGTH: 74
<212> TYPE: DNA
<213> ORGANISM: Artificial Sequence
<220> FEATURE:
<223> OTHER INFORMATION: SOEing primer

<400> SEQUENCE: 20
cccgcaaaga acgtggcgtt aaagcagatt ccgtattgat agtaaccata gctgtttcct      60
gtgtgaacag tact                                                        74

<210> SEQ ID NO 21
<211> LENGTH: 19
<212> TYPE: DNA
<213> ORGANISM: Artificial Sequence
<220> FEATURE:
<223> OTHER INFORMATION: Sequencing primer

<400> SEQUENCE: 21
cattcttctt acttttatg                                                   19

<210> SEQ ID NO 22
<211> LENGTH: 20
<212> TYPE: DNA
<213> ORGANISM: Artificial Sequence
<220> FEATURE:
<223> OTHER INFORMATION: Sequencing primer

<400> SEQUENCE: 22
ctggtcagca caaagtgatc                                                  20

<210> SEQ ID NO 23
<211> LENGTH: 144
<212> TYPE: DNA
<213> ORGANISM: Artificial Sequence
<220> FEATURE:
<223> OTHER INFORMATION: SOEing primer

<400> SEQUENCE: 23
cgaagcagct ccagcctaca cctttggcag tttattcttg acatgtagtg aggggctgg       60 tataatcaca tagtactgtt cacacaggaa acagctatgc aagcctattt tgaccagctc     120
gatcgcgttc gttatgaagg ctca                                            144

<210> SEQ ID NO 24
<211> LENGTH: 78
<212> TYPE: DNA
```

```
<213> ORGANISM: Artificial Sequence
<220> FEATURE:
<223> OTHER INFORMATION: SOEing primer

<400> SEQUENCE: 24
ttgttgcgca attgtactta ttgcattttt ctcttcgagg aattacccag tttcatcaat    60
tccggggatc cgtcgacc                                                 78

<210> SEQ ID NO 25
<211> LENGTH: 20
<212> TYPE: DNA
<213> ORGANISM: Artificial Sequence
<220> FEATURE:
<223> OTHER INFORMATION: SOEing primer

<400> SEQUENCE: 25
aactcaaatg cgacatctgc                                               20

<210> SEQ ID NO 26
<211> LENGTH: 20
<212> TYPE: DNA
<213> ORGANISM: Artificial Sequence
<220> FEATURE:
<223> OTHER INFORMATION: Sequencing primer

<400> SEQUENCE: 26
atgccttctt gtttggcttc                                               20

<210> SEQ ID NO 27
<211> LENGTH: 79
<212> TYPE: DNA
<213> ORGANISM: Artificial Sequence
<220> FEATURE:
<223> OTHER INFORMATION: SOEing primer

<400> SEQUENCE: 27
tgatgaaact gggtaattcc tcgaagagaa aaatgcaata agtacaattg cgcaacaagt    60
gtaggctgga gctgcttcg                                                79

<210> SEQ ID NO 28
<211> LENGTH: 99
<212> TYPE: DNA
<213> ORGANISM: Artificial Sequence
<220> FEATURE:
<223> OTHER INFORMATION: SOEing primer

<400> SEQUENCE: 28
catagctgtt tcctgtgtga acagtactca gttattatat catccggaaa tatctgtgtc    60
aagaataaac tcccacatga ttccggggat ccgtcgacc                          99

<210> SEQ ID NO 29
<211> LENGTH: 97
<212> TYPE: DNA
<213> ORGANISM: Artificial Sequence
<220> FEATURE:
<223> OTHER INFORMATION: SOEing primer

<400> SEQUENCE: 29
gacttctttg gcgtgtgcag caacgttggt aagcaggagt gaggtgcaaa gggtgagtag    60
aatgttcttt attttcatag ctgtttcctg tgtgaac                            97

<210> SEQ ID NO 30
<211> LENGTH: 20
```

```
<212> TYPE: DNA
<213> ORGANISM: Artificial Sequence
<220> FEATURE:
<223> OTHER INFORMATION: Sequencing primer

<400> SEQUENCE: 30
aactcaaatg cgacatctgc                                                       20

<210> SEQ ID NO 31
<211> LENGTH: 20
<212> TYPE: DNA
<213> ORGANISM: Artificial Sequence
<220> FEATURE:
<223> OTHER INFORMATION: Sequencing primer

<400> SEQUENCE: 31
atgccttctt gtttggcttc                                                       20

<210> SEQ ID NO 32
<211> LENGTH: 42
<212> TYPE: DNA
<213> ORGANISM: Artificial Sequence
<220> FEATURE:
<223> OTHER INFORMATION: Synthetic construct MutS A1R

<400> SEQUENCE: 32
ctctcatccg ccaaaacagc ccataaccca tgagtgcaat ag                              42

<210> SEQ ID NO 33
<211> LENGTH: 29
<212> TYPE: DNA
<213> ORGANISM: Artificial Sequence
<220> FEATURE:
<223> OTHER INFORMATION: Synthetic construct Cm R

<400> SEQUENCE: 33
ccgttttcac catgggcaaa tattatacg                                             29

<210> SEQ ID NO 34
<211> LENGTH: 45
<212> TYPE: DNA
<213> ORGANISM: Artificial Sequence
<220> FEATURE:
<223> OTHER INFORMATION: Synthetic construct MutS A5F

<400> SEQUENCE: 34
gtataatcac atagtactgt tttacaccag gctcttcaag cgata                           45

<210> SEQ ID NO 35
<211> LENGTH: 21
<212> TYPE: DNA
<213> ORGANISM: Artificial Sequence
<220> FEATURE:
<223> OTHER INFORMATION: Synthetic construct pSIM5 UP

<400> SEQUENCE: 35
cagtgcgtcc tgctgatgtg c                                                     21

<210> SEQ ID NO 36
<211> LENGTH: 21
<212> TYPE: DNA
<213> ORGANISM: Artificial Sequence
<220> FEATURE:
<223> OTHER INFORMATION: Synthetic construct araF-F

<400> SEQUENCE: 36
```

```
gctctcatta tacgtgttct g                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic construct araF-R

<400> SEQUENCE: 37
cctcaaaccc taaatccttc c                                              21

<210> SEQ ID NO 38
<211> LENGTH: 20
<212> TYPE: DNA
<213> ORGANISM: Artificial Sequence
<220> FEATURE:
<223> OTHER INFORMATION: Synthetic construct xylA-F

<400> SEQUENCE: 38
aactcaaatg cgacatctgc                                                20

<210> SEQ ID NO 39
<211> LENGTH: 20
<212> TYPE: DNA
<213> ORGANISM: Artificial Sequence
<220> FEATURE:
<223> OTHER INFORMATION: Synthetic construct xylA-R

<400> SEQUENCE: 39
atgccttctt gtttggcttc                                                20

<210> SEQ ID NO 40
<211> LENGTH: 21
<212> TYPE: DNA
<213> ORGANISM: Artificial Sequence
<220> FEATURE:
<223> OTHER INFORMATION: Synthetic construct araE SNP-F

<400> SEQUENCE: 40
gctataactg aacgctgtat c                                              21

<210> SEQ ID NO 41
<211> LENGTH: 20
<212> TYPE: DNA
<213> ORGANISM: Artificial Sequence
<220> FEATURE:
<223> OTHER INFORMATION: Synthetic construct araE SNP-R

<400> SEQUENCE: 41
ctgctttaac gccacgttct                                                20

<210> SEQ ID NO 42
<211> LENGTH: 20
<212> TYPE: DNA
<213> ORGANISM: Artificial Sequence
<220> FEATURE:
<223> OTHER INFORMATION: Synthetic construct ybjG-F

<400> SEQUENCE: 42
ccacgattgc agacgttgat                                                20

<210> SEQ ID NO 43
<211> LENGTH: 20
<212> TYPE: DNA
<213> ORGANISM: Artificial Sequence
```

```
<220> FEATURE:
<223> OTHER INFORMATION: Synthetic construct ybjG-R

<400> SEQUENCE: 43
cgccagactc ggctccgtgg                                                      20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct thiC-F

<400> SEQUENCE: 44
taaatgcgtt ttgagttggg                                                      20

<210> SEQ ID NO 45
<211> LENGTH: 20
<212> TYPE: DNA
<213> ORGANISM: Artificial Sequence
<220> FEATURE:
<223> OTHER INFORMATION: Synthetic construct thiC-R

<400> SEQUENCE: 45
atggattact acgattccag                                                      20

<210> SEQ ID NO 46
<211> LENGTH: 21
<212> TYPE: DNA
<213> ORGANISM: Artificial Sequence
<220> FEATURE:
<223> OTHER INFORMATION: Synthetic construct pyrE-F

<400> SEQUENCE: 46
gggccaaaca gcagatcgaa c                                                    21

<210> SEQ ID NO 47
<211> LENGTH: 20
<212> TYPE: DNA
<213> ORGANISM: Artificial Sequence
<220> FEATURE:
<223> OTHER INFORMATION: Synthetic construct pyrE-R

<400> SEQUENCE: 47
gtcggaattg tgaacggcga                                                      20

<210> SEQ ID NO 48
<211> LENGTH: 33
<212> TYPE: DNA
<213> ORGANISM: Artificial Sequence
<220> FEATURE:
<223> OTHER INFORMATION: Primer for cloning xylose reductase plasmid

<400> SEQUENCE: 48
gcgcatatgt caagcccact tttaacttta aac                                       33

<210> SEQ ID NO 49
<211> LENGTH: 36
<212> TYPE: DNA
<213> ORGANISM: Artificial Sequence
<220> FEATURE:
<223> OTHER INFORMATION: Primer for cloning xylose reductase plasmid

<400> SEQUENCE: 49
cgcggatcct taaataaatg ttggaatatt gtaacc                                    36
```

<210> SEQ ID NO 50
<211> LENGTH: 975
<212> TYPE: DNA
<213> ORGANISM: Artificial Sequence
<220> FEATURE:
<223> OTHER INFORMATION: Nucleotide sequence of araF delta11-15

<400> SEQUENCE: 50

```
atgcacaaat tactaaagc cctggcagcc gttatgtcac aatccgctat ggcggagaac      60
ctgaagctcg gttttctggt gaagcaaccg gaagagccgt ggttccagac cgaatggaag    120
tttgccgata agccgggaa ggatttaggg tttgaggtta ttaagattgc cgtgccggat     180
ggcgaaaaaa cattgaacgc gatcgacagc ctggctgcca gtggcgcaaa aggtttcgtt    240
atttgtactc cggaccccaa actcggctct gccatcgtcg cgaaagcgcg tggctacgat    300
atgaaagtca ttgccgtgga tgaccagttt gttaacgcca aggtaagcc aatggatacc    360
gttccgctgg tgatgatggc ggcgactaaa attggcgaac gtcagggcca ggaactgtat    420
aaagagatgc agaaacgtgg ctgggatgtc aaagaaagcg cggtgatggc gattaccgcc    480
aacgaactgg ataccgcccg ccgccgtact acgggatcta tggatgcgct gaaagcggcc    540
ggattcccgg aaaacaaat ttatcaggta cctaccaaat ctaacgacat cccgggggca    600
tttgacgctg ccaactcaat gctggttcaa catccggaag ttaaacattg gctgatcgtc    660
ggtatgaacg acagcaccgt gctgggcggc gtacgcgcga cggaaggtca gggctttaaa    720
gcggccgata tcatcggcat tggcattaac ggtgtggatg cggtgagcga actgtctaaa    780
gcacaggcaa ccggcttcta cggttccctg ctgccaagcc cggacgtaca tggctataaa    840
tccagcgaaa tgctttacaa ctgggtagca aaagacgttg aaccgccaaa atttaccgaa    900
gttaccgacg tggtactgat cacgcgtgac aactttaaag aagaactgga gaaaaaaggt    960
ttaggcggta agtaa                                                     975
```

<210> SEQ ID NO 51
<211> LENGTH: 198
<212> TYPE: PRT
<213> ORGANISM: Artificial Sequence
<220> FEATURE:
<223> OTHER INFORMATION: amino acid sequence of araF delta11-15

<400> SEQUENCE: 51

```
Met Leu Glu Asn Leu Asn Leu Ser Leu Phe Ser Leu Ile Asn Ala Thr
  1               5                  10                  15

Pro Asp Ser Ala Pro Trp Met Ile Ser Leu Ala Ile Phe Ile Ala Lys
             20                  25                  30

Asp Leu Ile Thr Val Val Pro Leu Leu Ala Val Val Leu Trp Leu Trp
         35                  40                  45

Gly Leu Thr Ala Gln Arg Gln Leu Val Ile Lys Ile Ala Ile Ala Leu
     50                  55                  60

Ala Val Ser Leu Phe Val Ser Trp Thr Met Gly His Leu Phe Pro His
 65                  70                  75                  80

Asp Arg Pro Phe Val Glu Asn Ile Gly Tyr Asn Phe Leu His His Ala
                 85                  90                  95

Ala Asp Gly Ser Phe Pro Ser Asp His Gly Thr Val Ile Phe Thr Phe
            100                 105                 110

Ala Leu Ala Phe Leu Cys Trp His Arg Leu Trp Ser Gly Ser Leu Leu
        115                 120                 125

Met Val Leu Ala Val Val Ile Ala Trp Ser Arg Val Tyr Leu Gly Val
```

His Trp Pro Leu Asp Met Leu Gly Gly Leu Leu Ala Gly Met Ile Gly
145                 150                 155                 160

Cys Leu Ser Ala Gln Ile Ile Trp Gln Ala Met Gly His Lys Leu Tyr
            165                 170                 175

Gln Arg Leu Gln Ser Trp Tyr Arg Val Cys Phe Ala Leu Pro Ile Arg
        180                 185                 190

Lys Gly Trp Val Arg Asp
        195

<210> SEQ ID NO 52
<211> LENGTH: 1523
<212> TYPE: DNA
<213> ORGANISM: Artificial Sequence
<220> FEATURE:
<223> OTHER INFORMATION: nucleotide sequence of araEL126*

<400> SEQUENCE: 52

| | | | | | |
|---|---|---|---|---|---|
| atgtcgcagc | aatttaatcc | atatttatgc | tgtttccgac | ctgacacctg | cgtgagttgt | 60 |
| tcacgtattt | tttcactatg | tcttactctc | tgctggcagg | aaaaaatggt | tactatcaat | 120 |
| acggaatctg | ctttaacgcc | acgttctttg | cgggatacgc | ggcgtatgaa | tatgtttgtt | 180 |
| tcggtagctg | ctgcggtcgc | aggattgtta | tttggtcttg | atatcggcgt | aatcgccgga | 240 |
| gcgttgccgt | tcattaccga | tcactttgtg | ctgaccagtc | gtttgcagga | atgggtggtt | 300 |
| agtagcatga | tgctcggtgc | agcaattggt | gcgctgttta | atggttggct | gtcgttccgc | 360 |
| ctggggcgta | atacatcctg | atggcggggg | ccatcctgtt | tgtactcggt | tctataqggt | 420 |
| ccgcttttgc | gaccagcgta | gagatgttaa | tcgccgctcg | tgtggtgctg | ggcattgctg | 480 |
| tcgggatcgc | gtcttacacc | gctcctctgt | atctttctga | aatggcaagt | gaaaacgttc | 540 |
| gcggtaagat | gatcagtatg | taccagttga | tggtcacact | cggcatcgtg | ctggcgtttt | 600 |
| tatccgatac | agcgttcagt | tatagcggta | actggcgcgc | aatgtggggg | ttcttgcttt | 660 |
| taccagcagt | tctgctgatt | attctggtag | tcttcctgcc | aaatagcccg | cgctggctgg | 720 |
| cggaaaaggg | gcgtcatatt | gaggcggaag | aagtattgcg | tatgctgcgc | gatacgtcgg | 780 |
| aaaaagcgcg | agaagaactc | aacgaaattc | gtgaaagcct | gaagttaaaa | cagggcggtt | 840 |
| gggcactgtt | taagatcaac | cgtaacgtcc | gtcgtgctgt | gtttctcggt | atgttgttgc | 900 |
| aggcgatgca | gcagtttacc | ggtatgaaca | tcatcatgta | ctacgcgccg | cgtatcttca | 960 |
| aaatggcggg | ctttacgacc | acagaacaac | agatgattgc | gactctggtc | gtagggctga | 1020 |
| cctttatgtt | cgccacctttt | attgcggtgt | ttacggtaga | taaagcaggg | cgtaaaccgg | 1080 |
| ctctgaaaat | tggtttcagc | gtgatggcgt | taggcactct | ggtgctgggc | tattgcctga | 1140 |
| tgcagtttga | taacggtacg | gcttccagtg | gcttgtcctg | gctctctgtt | ggcatgacga | 1200 |
| tgatgtgtat | tgccggttat | gcgatgagcg | ccgcgccagt | ggtgtggatc | ctgtgctctg | 1260 |
| aaattcagcc | gctgaaatgc | gcgatttcg | gtattacctg | ttcgaccacc | acgaactggg | 1320 |
| tgtcgaatat | gattatcggc | gcgaccttcc | tgacactgct | tgatagcatt | ggcgctgccg | 1380 |
| gtacgttctg | gctctacact | gcgctgaaca | ttgcgtttgt | gggcattact | ttctggctca | 1440 |
| ttccggaaac | caaaaatgtc | acgctggaac | atatcgaacg | caaactgatg | gcaggcgaga | 1500 |
| agttgagaaa | tatcggcgtc | tga | | | | 1523 |

<210> SEQ ID NO 53
<211> LENGTH: 91

<212> TYPE: PRT
<213> ORGANISM: Artificial Sequence
<220> FEATURE:
<223> OTHER INFORMATION: amino acid sequence of araEL126*

<400> SEQUENCE: 53

Met Val Thr Ile Asn Thr Glu Ser Ala Leu Thr Pro Arg Ser Leu Arg
 1               5                  10                  15

Asp Thr Arg Arg Met Asn Met Phe Val Ser Val Ala Ala Ala Val Ala
             20                  25                  30

Gly Leu Leu Phe Gly Leu Asp Ile Gly Val Ile Ala Gly Ala Leu Pro
         35                  40                  45

Phe Ile Thr Asp His Phe Val Leu Thr Ser Arg Leu Gln Glu Trp Val
     50                  55                  60

Val Ser Ser Met Met Leu Gly Ala Ala Ile Gly Ala Leu Phe Asn Gly
 65                  70                  75                  80

Trp Leu Ser Phe Arg Leu Gly Arg Asn Thr Ala
                 85                  90

<210> SEQ ID NO 54
<211> LENGTH: 60
<212> TYPE: DNA
<213> ORGANISM: Artificial Sequence
<220> FEATURE:
<223> OTHER INFORMATION: nucleotide sequence of thiCup

<400> SEQUENCE: 54
atcaggttcc gcggatcccg aataaacggt atcagccagt taaggcactc cgacaagaaa    60

<210> SEQ ID NO 55
<211> LENGTH: 69
<212> TYPE: DNA
<213> ORGANISM: Artificial Sequence
<220> FEATURE:
<223> OTHER INFORMATION: nucleotide sequence of xylAcp25

<400> SEQUENCE: 55
ctttggcagt ttattcttga catgtagtga gggggctggt ataatcacat agtactttc    60 acacaggaa                                                            69

<210> SEQ ID NO 56
<211> LENGTH: 597
<212> TYPE: DNA
<213> ORGANISM: Artificial Sequence
<220> FEATURE:
<223> OTHER INFORMATION: nucleotide sequence of ybjGD99G

<400> SEQUENCE: 56
atgctggaaa atttgaatct ctctctattc tctcttatta acgcgacgcc agactcggct    60
ccgtggatga tctcgttggc gatttttatt gctaaagatt tgattaccgt ggtgccgttg   120
ctggccgtgg tactttggtt gtgggggctt acagcacaac ggcaactggt gataaaaatc   180
gctatcgcgc tggcggtcag cctgtttgtg tcctggacga tgggacatct ttttccgcac   240
gaccgaccct ttgtcgaaaa tatcggctat aacttcctgc atcatgcggc ggatggctca   300
ttcccaagcg atcacggtac ggtgattttc acctttgcac tggcattttt atgctggcat   360
cgcctgtggt ccggctcact tttaatggtg ctggccgtcg tcattgcctg gtcgcgcgtt   420
tatcttggcg tccactggcc gctggatatg ctcggtggat gctggcagg atgattggc    480 tgccttagtg cccagattat ctggcaagcg atggggcata aactctatca acgtctgcaa   540
tcgtggtatc gcgtctgttt tgcattaccg atccgcaaag gctgggtgcg tgactga 597

<210> SEQ ID NO 57
<211> LENGTH: 198
<212> TYPE: PRT
<213> ORGANISM: Artificial Sequence
<220> FEATURE:
<223> OTHER INFORMATION: amino acid sequence of ybjGD99G

<400> SEQUENCE: 57

```
Met Leu Glu Asn Leu Asn Leu Ser Leu Phe Ser Leu Ile Asn Ala Thr
 1               5                  10                  15

Pro Asp Ser Ala Pro Trp Met Ile Ser Leu Ala Ile Phe Ile Ala Lys
            20                  25                  30

Asp Leu Ile Thr Val Val Pro Leu Leu Ala Val Val Leu Trp Leu Trp
        35                  40                  45

Gly Leu Thr Ala Gln Arg Gln Leu Val Ile Lys Ile Ala Ile Ala Leu
    50                  55                  60

Ala Val Ser Leu Phe Val Ser Trp Thr Met Gly His Leu Phe Pro His
65                  70                  75                  80

Asp Arg Pro Phe Val Glu Asn Ile Gly Tyr Asn Phe Leu His His Ala
                85                  90                  95

Ala Asp Gly Ser Phe Pro Ser Asp His Gly Thr Val Ile Phe Thr Phe
            100                 105                 110

Ala Leu Ala Phe Leu Cys Trp His Arg Leu Trp Ser Gly Ser Leu Leu
        115                 120                 125

Met Val Leu Ala Val Val Ile Ala Trp Ser Arg Val Tyr Leu Gly Val
    130                 135                 140

His Trp Pro Leu Asp Met Leu Gly Gly Leu Leu Ala Gly Met Ile Gly
145                 150                 155                 160

Cys Leu Ser Ala Gln Ile Ile Trp Gln Ala Met Gly His Lys Leu Tyr
                165                 170                 175

Gln Arg Leu Gln Ser Trp Tyr Arg Val Cys Phe Ala Leu Pro Ile Arg
            180                 185                 190

Lys Gly Trp Val Arg Asp
        195
```

<210> SEQ ID NO 58
<211> LENGTH: 1524
<212> TYPE: DNA
<213> ORGANISM: Artificial Sequence
<220> FEATURE:
<223> OTHER INFORMATION: nucleotide sequence of araES911

<400> SEQUENCE: 58
atgtcgcagc aatttaatcc atatttatgc tgtttccgac tgacacctg cgtgagttgt      60 tcacgtattt tttcactatg tcttactctc tgctggcagg aaaaaatggt tactatcaat     120
acggaatctg ctttaacgcc acgttctttg cgggatacgc ggcgtatgaa tatgtttgtt    180
tcggtagctg ctgcggtcgc aggattgtta tttggtcttg atatcggcgt aatcgccgga   240
gcgttgccgt tcattaccga tcactttgtg ctgaccagtc gtttgcagga atgggtggtt    300
agtagcatga tgctcggtgc agcaattggt gcgctgttta tggttggct gtcgttccgc    360 ctggggcgta atacatcct gatggcgggg gccatcctgt tgtactcgg ttctataggg    420 tccgcttttg cgaccagcgt agagatgtta atcgccgctc gtgtggtgct gggcattgct    480
gtcgggatcg cgtcttacac cgtcctctg tatctttctg aaatggcaag tgaaaacgtt   540

```
cgcggtaaga tgatcagtat gtaccagttg atggtcacac tcggcatcgt gctggcgttt      600
ttatccgata cagcgttcag ttatagcggt aactggcgcg caatgttggg ggttcttgct      660
ttaccagcag ttctgctgat tattctggta gtcttcctgc aaatagccc gcgctggctg       720 gcggaaaagg ggcgtcatat tgaggcggaa gaagtattgc gtatgctgcg cgatacgtcg      780
gaaaaagcgc gagaagaact caacgaaatt cgtgaaagcc tgaagttaaa acagggcggt      840
tgggcactgt ttaagatcaa ccgtaacgtc cgtcgtgctg tgtttctcgg tatgttgttg      900
caggcgatgc agcagtttac cggtatgaac atcatcatgt actacgcgcc gcgtatcttc      960
aaaatggcgg gctttacgac cacagaacaa cagatgattg cgactctggt cgtagggctg     1020
acctttatgt tcgccacctt tattgcggtg tttacggtag ataaagcagg gcgtaaaccg     1080
gctctgaaaa ttggtttcag cgtgatggcg ttaggcactc tggtgctggg ctattgcctg     1140
atgcagtttg ataacggtac ggcttccagt ggcttgtcct ggctctctgt tggcatgacg     1200
atgatgtgta ttgccggtta tgcgatgagc gccgcgccag tggtgtggat cctgtgctct     1260
gaaattcagc cgctgaaatg ccgcgatttc ggtattacct gttcgaccac cacgaactgg     1320
gtgtcgaata tgattatcgg cgcgaccttc ctgacactgc ttgatagcat tggcgctgcc     1380
ggtacgttct ggctctacac tgcgctgaac attgcgtttg tgggcattac tttctggctc     1440
attccggaaa ccaaaaatgt cacgctggaa catatcgaac gcaaactgat ggcaggcgag     1500
aagttgagaa atatcggcgt ctga                                             1524
```

<210> SEQ ID NO 59
<211> LENGTH: 472
<212> TYPE: PRT
<213> ORGANISM: Artificial Sequence
<220> FEATURE:
<223> OTHER INFORMATION: amino acid sequence of araES911

<400> SEQUENCE: 59

```
Met Val Thr Ile Asn Thr Glu Ser Ala Leu Thr Pro Arg Ser Leu Arg
  1               5                  10                  15

Asp Thr Arg Arg Met Asn Met Phe Val Ser Val Ala Ala Val Ala
             20                  25                  30

Gly Leu Leu Phe Gly Leu Asp Ile Gly Val Ile Ala Gly Ala Leu Pro
         35                  40                  45

Phe Ile Thr Asp His Phe Val Leu Thr Ser Arg Leu Gln Glu Trp Val
     50                  55                  60

Val Ser Ser Met Met Leu Gly Ala Ala Ile Gly Ala Leu Phe Asn Gly
 65                  70                  75                  80

Trp Leu Ser Phe Arg Leu Gly Arg Lys Tyr Ile Leu Met Ala Gly Ala
                 85                  90                  95

Ile Leu Phe Val Leu Gly Ser Ile Gly Ser Ala Phe Ala Thr Ser Val
            100                 105                 110

Glu Met Leu Ile Ala Ala Arg Val Val Leu Gly Ile Ala Val Gly Ile
        115                 120                 125

Ala Ser Tyr Thr Ala Pro Leu Tyr Leu Ser Glu Met Ala Ser Glu Asn
    130                 135                 140

Val Arg Gly Lys Met Ile Ser Met Tyr Gln Leu Met Val Thr Leu Gly
145                 150                 155                 160

Ile Val Leu Ala Phe Leu Ser Asp Thr Ala Phe Ser Tyr Ser Gly Asn
                165                 170                 175

Trp Arg Ala Met Leu Gly Val Leu Ala Leu Pro Ala Val Leu Leu Ile
            180                 185                 190
```

```
Ile Leu Val Val Phe Leu Pro Asn Ser Pro Arg Trp Leu Ala Glu Lys
            195                 200                 205

Gly Arg His Ile Glu Ala Glu Glu Val Leu Arg Met Leu Arg Asp Thr
        210                 215                 220

Ser Glu Lys Ala Arg Glu Glu Leu Asn Glu Ile Arg Glu Ser Leu Lys
225                 230                 235                 240

Leu Lys Gln Gly Gly Trp Ala Leu Phe Lys Ile Asn Arg Asn Val Arg
                245                 250                 255

Arg Ala Val Phe Leu Gly Met Leu Leu Gln Ala Met Gln Gln Phe Thr
                260                 265                 270

Gly Met Asn Ile Ile Met Tyr Tyr Ala Pro Arg Ile Phe Lys Met Ala
            275                 280                 285

Gly Phe Thr Thr Thr Glu Gln Gln Met Ile Ala Thr Leu Val Val Gly
        290                 295                 300

Leu Thr Phe Met Phe Ala Thr Phe Ile Ala Val Phe Thr Val Asp Lys
305                 310                 315                 320

Ala Gly Arg Lys Pro Ala Leu Lys Ile Gly Phe Ser Val Met Ala Leu
                325                 330                 335

Gly Thr Leu Val Leu Gly Tyr Cys Leu Met Gln Phe Asp Asn Gly Thr
            340                 345                 350

Ala Ser Ser Gly Leu Ser Trp Leu Ser Val Gly Met Thr Met Met Cys
            355                 360                 365

Ile Ala Gly Tyr Ala Met Ser Ala Ala Pro Val Val Trp Ile Leu Cys
            370                 375                 380

Ser Glu Ile Gln Pro Leu Lys Cys Arg Asp Phe Gly Ile Thr Cys Ser
385                 390                 395                 400

Thr Thr Thr Asn Trp Val Ser Asn Met Ile Ile Gly Ala Thr Phe Leu
                405                 410                 415

Thr Leu Leu Asp Ser Ile Gly Ala Ala Gly Thr Phe Trp Leu Tyr Thr
                420                 425                 430

Ala Leu Asn Ile Ala Phe Val Gly Ile Thr Phe Trp Leu Ile Pro Glu
            435                 440                 445

Thr Lys Asn Val Thr Leu Glu His Ile Glu Arg Lys Leu Met Ala Gly
        450                 455                 460

Glu Lys Leu Arg Asn Ile Gly Val
465                 470

<210> SEQ ID NO 60
<211> LENGTH: 59
<212> TYPE: DNA
<213> ORGANISM: Artificial Sequence
<220> FEATURE:
<223> OTHER INFORMATION: nucleotide sequence of pyrEup

<400> SEQUENCE: 60
tcatcttact tttctacaga caaaaaaaag cgactcatca gtcgccttaa aaatcagtt      59

<210> SEQ ID NO 61
<211> LENGTH: 60
<212> TYPE: DNA
<213> ORGANISM: Artificial
<220> FEATURE:
<223> OTHER INFORMATION: nucleotide sequence of pyrE upstream region of
      MG1655

<400> SEQUENCE: 61
tcatcttact tttctacaga caaaaaaaag gcgactcatc agtcgccttaa aaatcagtt     60
```

<210> SEQ ID NO 62
<211> LENGTH: 60
<212> TYPE: DNA
<213> ORGANISM: Artificial
<220> FEATURE:
<223> OTHER INFORMATION: nucleotide sequence of pyrE upstream region of
      AXcp

<400> SEQUENCE: 62
tcatcttact tttctacaga caaaaaaaag gcgactcatc agtcgcctta aaaatcagtt      60

<210> SEQ ID NO 63
<211> LENGTH: 60
<212> TYPE: DNA
<213> ORGANISM: Artificial
<220> FEATURE:
<223> OTHER INFORMATION: nucleotide sequence of pyrE upstream region of
      AXcpX50

<400> SEQUENCE: 63
tcatcttact tttctacaga caaaaaaaag gcgactcatc agtcgcctta aaaatcagtt      60

<210> SEQ ID NO 64
<211> LENGTH: 59
<212> TYPE: DNA
<213> ORGANISM: Artificial
<220> FEATURE:
<223> OTHER INFORMATION: nucleotide sequence of pyrE upstream region of
      AXcpAX50

<400> SEQUENCE: 64
tcatcttact tttctacaga caaaaaaaag cgactcatca gtcgccttaa aaatcagtt       59

<210> SEQ ID NO 65
<211> LENGTH: 45
<212> TYPE: DNA
<213> ORGANISM: Artificial
<220> FEATURE:
<223> OTHER INFORMATION: nucleotide sequence of ybjG coding region of
      MG1655

<400> SEQUENCE: 65
ttcctgcatc atgcggcgga tgactcattc ccaagcgatc acggt                      45

<210> SEQ ID NO 66
<211> LENGTH: 45
<212> TYPE: DNA
<213> ORGANISM: Artificial
<220> FEATURE:
<223> OTHER INFORMATION: nucleotide sequence of ybjG coding region of
      AXcp

<400> SEQUENCE: 66
ttcctgcatc atgcggcgga tgactcattc ccaagcgatc acggt                      45

<210> SEQ ID NO 67
<211> LENGTH: 45
<212> TYPE: DNA
<213> ORGANISM: Artificial
<220> FEATURE:
<223> OTHER INFORMATION: nucleotide sequence of ybjG coding region of
      AXcpX50

<400> SEQUENCE: 67
ttcctgcatc atgcggcgga tgactcattc ccaagcgatc acggt                      45

<210> SEQ ID NO 68
<211> LENGTH: 45
<212> TYPE: DNA
<213> ORGANISM: Artificial
<220> FEATURE:
<223> OTHER INFORMATION: nucleotide sequence of ybjG coding region of
      AXcpAX50

<400> SEQUENCE: 68
ttcctgcatc atgcggcgga tggctcattc ccaagcgatc acggt                45

<210> SEQ ID NO 69
<211> LENGTH: 45
<212> TYPE: DNA
<213> ORGANISM: Artificial
<220> FEATURE:
<223> OTHER INFORMATION: nucleotide sequence of araE coding region of
      MG1655

<400> SEQUENCE: 69
ttccgcctgg ggcgtaaata cagcctgatg gcgggggcca tcctg                45

<210> SEQ ID NO 70
<211> LENGTH: 45
<212> TYPE: DNA
<213> ORGANISM: Artificial
<220> FEATURE:
<223> OTHER INFORMATION: nucleotide sequence of araE coding region of
      AXcp

<400> SEQUENCE: 70
ttccgcctgg ggcgtaaata cagcctgatg gcgggggcca tcctg                45

<210> SEQ ID NO 71
<211> LENGTH: 44
<212> TYPE: DNA
<213> ORGANISM: Artificial
<220> FEATURE:
<223> OTHER INFORMATION: nucleotide sequence of araE coding region of
      AXcpX50

<400> SEQUENCE: 71
ttccgcctgg ggcgtaatac agcctgatgg cgggggccat cctg                 44

<210> SEQ ID NO 72
<211> LENGTH: 45
<212> TYPE: DNA
<213> ORGANISM: Artificial
<220> FEATURE:
<223> OTHER INFORMATION: nucleotide sequence of araE coding region of
      AXcpAX50

<400> SEQUENCE: 72
ttccgcctgg ggcgtaaata catcctgatg gcgggggcca tcctg                45

<210> SEQ ID NO 73
<211> LENGTH: 60
<212> TYPE: DNA
<213> ORGANISM: Artificial
<220> FEATURE:
<223> OTHER INFORMATION: nucleotide sequence of thiC upstream region of
      MG1655

<400> SEQUENCE: 73
atcaggttcc gcggatcccg aataaacggt ctcagccagt taaggcactc cgacaagaaa    60

<210> SEQ ID NO 74
<211> LENGTH: 60
<212> TYPE: DNA
<213> ORGANISM: Artificial
<220> FEATURE:
<223> OTHER INFORMATION: nucleotide sequence of thiC upstream region of
      AXcp

<400> SEQUENCE: 74
atcaggttcc gcggatcccg aataaacggt ctcagccagt taaggcactc cgacaagaaa    60

<210> SEQ ID NO 75
<211> LENGTH: 60
<212> TYPE: DNA
<213> ORGANISM: Artificial
<220> FEATURE:
<223> OTHER INFORMATION: nucleotide sequence of thiC upstream region of
      AXcpX50

<400> SEQUENCE: 75
atcaggttcc gcggatcccg aataaacggt atcagccagt taaggcactc cgacaagaaa    60

<210> SEQ ID NO 76
<211> LENGTH: 60
<212> TYPE: DNA
<213> ORGANISM: Artificial
<220> FEATURE:
<223> OTHER INFORMATION: nucleotide sequence of thiC upstream region of
      AXcpAX50

<400> SEQUENCE: 76
atcaggttcc gcggatcccg aataaacggt ctcagccagt taaggcactc cgacaagaaa    60

<210> SEQ ID NO 77
<211> LENGTH: 45
<212> TYPE: DNA
<213> ORGANISM: Artificial
<220> FEATURE:
<223> OTHER INFORMATION: nucleotide sequence of araF coding region of
      MG1655

<400> SEQUENCE: 77
gccctggcag ccattggtct ggcagccgtt atgtcacaat ccgct                    45

<210> SEQ ID NO 78
<211> LENGTH: 45
<212> TYPE: DNA
<213> ORGANISM: Artificial
<220> FEATURE:
<223> OTHER INFORMATION: nucleotide sequence of araF coding region of
      AXcp

<400> SEQUENCE: 78
gccctggcag ccattggtct ggcagccgtt atgtcacaat ccgct                    45

<210> SEQ ID NO 79
<211> LENGTH: 30
<212> TYPE: DNA
<213> ORGANISM: Artificial
<220> FEATURE:
<223> OTHER INFORMATION: nucleotide sequence of araF coding region of
      AXcpX50

<400> SEQUENCE: 79
gccctggcag ccgttatgtc acaatccgct                                     30

<210> SEQ ID NO 80

-continued

<210> SEQ ID NO 80
<211> LENGTH: 45
<212> TYPE: DNA
<213> ORGANISM: Artificial
<220> FEATURE:
<223> OTHER INFORMATION: nucleotide sequence of araF coding region of
      AXcpAX50

<400> SEQUENCE: 80
gccctggcag ccattggtct ggcagccgtt atgtcacaat ccgct                45

<210> SEQ ID NO 81
<211> LENGTH: 69
<212> TYPE: DNA
<213> ORGANISM: Artificial
<220> FEATURE:
<223> OTHER INFORMATION: nucleotide sequence of reference xylAB CP25
      promoter region

<400> SEQUENCE: 81
ctttggcagt ttattcttga catgtagtga gggggctggt ataatcacat agtactgttc    60
acacaggaa                                                          69

<210> SEQ ID NO 82
<211> LENGTH: 69
<212> TYPE: DNA
<213> ORGANISM: Artificial
<220> FEATURE:
<223> OTHER INFORMATION: nucleotide sequence of xylAB CP25 promoter
      region of Axcp

<400> SEQUENCE: 82
ctttggcagt ttattcttga catgtagtga gggggctggt ataatcacat agtactgttc    60
acacaggaa                                                          69

<210> SEQ ID NO 83
<211> LENGTH: 69
<212> TYPE: DNA
<213> ORGANISM: Artificial
<220> FEATURE:
<223> OTHER INFORMATION: nucleotide sequence of xylAB CP25 promoter
      region of AxcpX50

<400> SEQUENCE: 83
ctttggcagt ttattcttga catgtagtga gggggctggt ataatcacat agtactttc     60 acacaggaa                                                          69

<210> SEQ ID NO 84
<211> LENGTH: 69
<212> TYPE: DNA
<213> ORGANISM: Artificial
<220> FEATURE:
<223> OTHER INFORMATION: nucleotide sequence of xylAB CP25 promoter
      region of AxcpAX50

<400> SEQUENCE: 84
ctttggcagt ttattcttga catgtagtga gggggctggt ataatcacat agtactttc     60 acacaggaa                                                          69

<210> SEQ ID NO 85
<211> LENGTH: 60
<212> TYPE: PRT
<213> ORGANISM: Artificial Sequence
<220> FEATURE:
<223> OTHER INFORMATION: partial amino acid sequence of AraE of of
      MG1655

-continued

<400> SEQUENCE: 85

Leu Asp Ile Gly Val Ile Ala Gly Ala Leu Pro Phe Ile Thr Asp His
1               5                   10                  15

Phe Val Leu Thr Ser Arg Leu Gln Glu Trp Val Val Ser Ser Met Met
            20                  25                  30

Leu Gly Ala Ala Ile Gly Ala Leu Phe Asn Gly Trp Leu Ser Phe Arg
        35                  40                  45

Leu Gly Arg Lys Tyr Ser Leu Met Ala Gly Ala Ile
    50                  55                  60

<210> SEQ ID NO 86
<211> LENGTH: 54
<212> TYPE: PRT
<213> ORGANISM: Artificial Sequence
<220> FEATURE:
<223> OTHER INFORMATION: partial amino acid sequence of AraE of AxcpX50

<400> SEQUENCE: 86

Leu Asp Ile Gly Val Ile Ala Gly Ala Leu Pro Phe Ile Thr Asp His
1               5                   10                  15

Phe Val Leu Thr Ser Arg Leu Gln Glu Trp Val Val Ser Ser Met Met
            20                  25                  30

Leu Gly Ala Ala Ile Gly Ala Leu Phe Asn Gly Trp Leu Ser Phe Arg
        35                  40                  45

Leu Gly Arg Lys Thr Ala
    50

<210> SEQ ID NO 87
<211> LENGTH: 60
<212> TYPE: PRT
<213> ORGANISM: Artificial Sequence
<220> FEATURE:
<223> OTHER INFORMATION: partial amino acid sequence of AraF of of
      MG1655

<400> SEQUENCE: 87

Met His Lys Phe Thr Lys Ala Leu Ala Ala Ile Gly Leu Ala Ala Val
1               5                   10                  15

Met Ser Gln Ser Ala Met Ala Glu Asn Leu Lys Leu Gly Phe Leu Val
            20                  25                  30

Lys Gln Pro Glu Glu Pro Trp Phe Gln Thr Glu Trp Lys Phe Ala Asp
        35                  40                  45

Lys Ala Gly Lys Asp Leu Gly Phe Glu Val Ile Lys
    50                  55                  60

<210> SEQ ID NO 88
<211> LENGTH: 55
<212> TYPE: PRT
<213> ORGANISM: Artificial Sequence
<220> FEATURE:
<223> OTHER INFORMATION: partial amino acid sequence of AraF of AxcpX50

<400> SEQUENCE: 88

Met His Lys Phe Thr Lys Ala Leu Ala Ala Val Met Ser Gln Ser Ala
1               5                   10                  15

Met Ala Glu Asn Leu Lys Leu Gly Phe Leu Val Lys Gln Pro Glu Glu
            20                  25                  30

Pro Trp Phe Gln Thr Glu Trp Lys Phe Ala Asp Lys Ala Gly Lys Asp
        35                  40                  45

Leu Gly Phe Glu Val Ile Lys
          50                  55

<210> SEQ ID NO 89
<211> LENGTH: 60
<212> TYPE: PRT
<213> ORGANISM: Artificial Sequence
<220> FEATURE:
<223> OTHER INFORMATION: partial amino acid sequence of AraE of of
      MG1655

<400> SEQUENCE: 89

Leu Gly Arg Lys Tyr Ser Leu Met Ala Gly Ala Ile Leu Phe Val Leu
  1               5                  10                  15

Gly Ser Ile Gly Ser Ala Phe Ala Thr Ser Val Glu Met Leu Ile Ala
             20                  25                  30

Ala Arg Val Val Leu Gly Ile Ala Val Gly Ile Ala Ser Tyr Thr Ala
         35                  40                  45

Pro Leu Tyr Leu Ser Glu Met Ala Ser Glu Asn Val
     50                  55                  60

<210> SEQ ID NO 90
<211> LENGTH: 60
<212> TYPE: PRT
<213> ORGANISM: Artificial Sequence
<220> FEATURE:
<223> OTHER INFORMATION: partial amino acid sequence of AraE of of
      AxcpX50

<400> SEQUENCE: 90

Leu Gly Arg Lys Tyr Ile Leu Met Ala Gly Ala Ile Leu Phe Val Leu
  1               5                  10                  15

Gly Ser Ile Gly Ser Ala Phe Ala Thr Ser Val Glu Met Leu Ile Ala
             20                  25                  30

Ala Arg Val Val Leu Gly Ile Ala Val Gly Ile Ala Ser Tyr Thr Ala
         35                  40                  45

Pro Leu Tyr Leu Ser Glu Met Ala Ser Glu Asn Val
     50                  55                  60

<210> SEQ ID NO 91
<211> LENGTH: 60
<212> TYPE: PRT
<213> ORGANISM: Artificial Sequence
<220> FEATURE:
<223> OTHER INFORMATION: partial amino acid sequence of YbjG of of
      MG1655

<400> SEQUENCE: 91

Ala Ile Ala Leu Ala Val Ser Leu Phe Val Ser Trp Thr Met Gly His
  1               5                  10                  15

Leu Phe Pro His Asp Arg Pro Phe Val Glu Asn Ile Gly Tyr Asn Phe
             20                  25                  30

Leu His His Ala Ala Asp Asp Ser Phe Pro Ser Asp His Gly Thr Val
         35                  40                  45

Ile Phe Thr Phe Ala Leu Ala Phe Leu Cys Trp His
     50                  55                  60

<210> SEQ ID NO 92
<211> LENGTH: 60
<212> TYPE: PRT
<213> ORGANISM: Artificial Sequence
<220> FEATURE:
<223> OTHER INFORMATION: partial amino acid sequence of YbjG of

```
    AxcpX50

<400> SEQUENCE: 92

Ala Ile Ala Leu Ala Val Ser Leu Phe Val Ser Trp Thr Met Gly His
 1               5                  10                  15

Leu Phe Pro His Asp Arg Pro Phe Val Glu Asn Ile Gly Tyr Asn Phe
            20                  25                  30

Leu His His Ala Ala Asp Gly Ser Phe Pro Ser Asp His Gly Thr Val
        35                  40                  45

Ile Phe Thr Phe Ala Leu Ala Phe Leu Cys Trp His
50                  55                  60
```

METHOD FOR PREPARING MUTANT *ESCHERICHIA COLI* CAPABLE OF SIMULTANEOUSLY UTILIZING GLUCOSE AND XYLOSE

FIELD OF THE INVENTION

The present invention relates to a method for preparing a mutant *E. coli* capable of simultaneously utilizing glucose and xylose. More particularly, the present invention relates to a method for preparing a mutant *E. coli* strain capable of simultaneously utilizing glucose and xylose, via genetic engineering and evolutionary adaptation; the mutant *E. coli* prepared using the same; and a method for producing a biofuel, a biologically active ingredient, a medicinal material or a chemical substance for the chemical industry using the mutant *E. coli*.

BACKGROUND OF THE INVENTION

With the depletion of petrochemical fuels, intensive worldwide attention has been paid to alternative energies. As one of the alternative energies, fuel ethanol can be converted from a cellulosic biomass. A tremendous quantity of cellulose is produced each year as they are fixed through photosynthesis. In addition, cellulose is regenerable. When account is taken of its regenerability and productivity, cellulose is very advantageous functionally and economically. These days, a lignocellulosic biomass is predominantly utilized out of the cellulosic biomass, and extensive research has been focused on the effective degradation of the ingredients of a lignocellulosic biomass including cellulose, hemicellulose, and lignin; additionally a search for new strains of cellulosic biomass producers, and saccharification and fermentation processes are being researched.

Production of cellulosic fuels may be largely divided into i) an enzymatic saccharification process of a biomass using at least three enzymes (endoglucanase, exoglucanase, and β-glucanase), and ii) a microbial fermentation process of the sugars thus obtained. Recently, there have been extensive studies on simultaneous saccharification and fermentation (SSF) that is designed to simultaneously perform an enzymatic saccharification process and a fermentation process in one reactor whereby a significant reduction can be brought about in facility cost and enzymatic inhibitory activity, resulting in an increase in the production efficiency of ethanol. Of the processes, the enzymatic saccharification process is the most costly. Thus, studies have been directed towards either the functional enhancement or the use reduction of the enzymes used in saccharification by developing fermentation strains of bacteria which produce pertinent enzymes. Particularly, a recent advance in bioengineering technology has allowed genes of saccharification-related enzymes to be introduced into and expressed in fermentation strains of bacteria, in order to develop strains of bacteria capable of simultaneously performing saccharification and fermentation. However, this strategy suffers from the disadvantage of being very low in the expression efficiency of exogenous genes such as saccharification-related genes, and having a negative influence on cell growth and metabolism upon overexpression. Hence, the focus of interest has been shifted from the introduction of exogenous genes to a modification in the regulation of pathways endogenous to fermentation strains.

*Escherichia coli* is regarded as an efficient means for the production of lignocellulosic fuels because it can utilize all of the sugars present in hydrolysates of a biomass. However, if a preferred sugar (e.g., glucose) exists in the hydrolysates, carbon catabolite repression (CCR), which accounts for the inhibition of synthesis of enzymes involved in catabolism of carbon sources other than the target, occurs with the consequent restriction of the potentiality of microorganisms. Sugars such as xylose and arabinose, although present in hydrolysates, cannot be metabolized until glucose is completely depleted. This preference for glucose disturbs fermentation processes thereby reducing the efficiency of the processes, and has a negative effect on downstream processes due to the accumulation of unutilized carbon sources. Sugar mixtures obtained from lignocellulosic hydrolysates are highly variable in composition, but with a predominance of glucose and xylose over other sugars. To improve the production of cellulosic fuels in terms of cost, efficiency and ease, there is a requirement for the development of a mutant *E. coli* which can utilize these two sugars simultaneously.

The simultaneous utilization of glucose and xylose has been demonstrated by some catabolite derepressed *E. coli* strains. Many studies have been focused on cAMP receptor protein (CRP), known as a global transcriptional regulator of CCR. Some *E. coli* strains with mutant CRP (CRP*) were found to partially deviate from the CCR control (Karimova, G., et al., Research in Microbiology, 2004, 155(2): 76-79; Nair, N. U., et al., Metabolic Engineering, 2010, 12(5): 462-468; Kimata, K., et al., Proceedings of the National Academy of Sciences of the Unites States of America, 1997, 94(24): 12914-12919; Inada, T., et al., Genes Cells, 1996, 1(3): 293-301). In addition, glucose phosphotransferase system (PTS)-devoid of *E. coli* was partially deprived of CCR, and the deletion of methylglyoxal synthase gene was helpful in regulating the pattern of utility of glucose. However, these methods cannot remove CCR to a sufficient enough extent to produce cellulosic biofuels, and accordingly, there still remains a need for new approaches.

Meanwhile, L-arabinose metabolism-related operons and genes, generally referred to as the ara operons, are gene sequence encoding enzymes needed for the catabolism of arabinose to xylulose 5-phosphate, an intermediate of the pentose phosphate pathway. Among the ara operons are the araBAD operon and the araFGH operon, and araE as an individual gene. Of them, araB codes for L-ribulokinase, araA for L-arabinose isomerase, araD for L-ribulose-5-phosphatase 4-epimerase; araF, araG and araH for respective arabinose ABC transporter subunits; and araE for arabinose/hydrogen ion symporter (Mayer, C. and W. Boos, Chapter 3.4.1, Hexose/Pentose and Hexitol/Pentitol Metabolism. In A. Böck, R. Curtiss III, J. B. Kaper, P. D. Karp, F. C. Neidhardt, T. Nyström, J. M. Slauch, C. L. Squires, and D. Ussery (ed.), EcoSal—*Escherichia coli* and *Salmonella*: Cellular and Molecular Biology. http://www.ecosal.org. ASM Press, Washington, D.C.).

Likewise, D-xylose metabolism-related operons and genes, which are generally called xyl operons, are gene sequence encoding enzymes needed for the catabolism of xylose to xylulose 5-phosphate, an intermediate of the pentose phosphate pathway. The xyl operon contains xylAB operon and xylGFH operon wherein xylA codes for D-xylose isomerase, xylB for xylulokinase, and xylF, xylG and xylH for respective D-xylose ABC transferase subunits (Mayer, C. and W. Boos, Chapter 3.4.1, Hexose/Pentose and Hexitol/Pentitol Metabolism. In A. Böck, R. Curtiss III, J. B. Kaper, P. D. Karp, F. C. Neidhardt, T. Nyström, J. M. Slauch, C. L. Squires, and D. Ussery (ed.), EcoSal—*Escherichia coli* and *Salmonella*: Cellular and Molecular Biology. http://www.e-cosal.org. ASM Press, Washington, D.C.)

Leading to the present invention, intensive and thorough research into the effective production of a biofuel, a biologically active ingredient, and a medicinal material from a biomass resulted in the finding that when inducible promoters of araBAD operon, araFGH operon, araE gene, xylAB operon, and xylGFH operon in a wild-type *E. coli* were changed into constitutive ones, the resulting mutant *E. coli* grown in a xylose minimal medium or an arabinose and xylose minimal medium, could utilize glucose and xylose, simultaneously.

SUMMARY OF THE INVENTION

Accordingly, it is an object of the present invention to provide a method for preparing mutant *Escherichia coli* capable of simultaneously utilizing glucose and xylose.

It is another object of the present invention to provide a mutant *E. coli* capable of simultaneously utilizing glucose and xylose, prepared using the method.

It is a further object of the present invention to provide a method for producing a biofuel, a biologically active ingredient, a medicinal material, or a chemical substance for the chemical industry from a biomass.

In accordance with an aspect thereof, the present invention provides a method for preparing a mutant *E. coli* capable of simultaneously utilizing glucose and xylose from a wild-type *E. coli*, comprising: (1) replacing inducible promoters of araBAD operon, araFGH operon, araE gene, xylAB operon, and xylFGH operon of the wild-type *E. coli* with respective constitutive promoters; and (2) growing the promoter-replaced *E. coli* in a xylose minimal medium or an arabinose and xylose minimal medium of for 10 days or longer.

In accordance with another aspect thereof, the present invention provides a mutant *E. coli* strain, capable of simultaneously utilizing glucose and xylose, prepared by replacing inducible promoters of araBAD operon, araFGH operon, araE gene, xylAB operon, and xylFGH operon of a wild-type *E. coli* with respective constitutive promoters, and growing the promoter-replaced *E. coli* in a xylose minimal medium or an arabinose and xylose minimal medium for 10 days or longer.

In accordance with a further aspect thereof, the present invention provides a method for producing a biofuel, a biologically active ingredient, a medicinal material, or a chemical substance for the chemical industry from a biomass by using a mutant *E. coli* capable of simultaneously utilizing glucose and xylose, said mutant *E. coli* being prepared by replacing inducible promoters of araBAD operon, araFGH operon, araE gene, xylAB operon, and xylFGH operon of a wild-type *E. coli* with respective constitutive promoters, and growing the promoter-replaced *E. coli* in a xylose minimal medium or an arabinose and xylose minimal medium for 10 days or longer.

Having the ability to simultaneously utilize glucose and xylose as opposed to a wild-type *E. coli*, the mutant *E. coli* according to the present invention can reduce the time taken by biochemical processes for the production of a biofuel, a biologically active ingredient, a medicinal material, a chemical substance for the chemical industry from a biomass, and thus can improve productivity.

BRIEF DESCRIPTION OF THE DRAWINGS

The above and other objects and features of the present invention will become apparent from the following description of the invention, when taken in conjunction with the accompanying drawings, which respectively show:

FIG. 10 compares nucleotide sequence alignments in modified DNA regions of individual strains, MG1655, AXcp, AXcpX50 and AXcpAX50;

FIG. 11 shows peptide sequence alignments of the mutant genes of individual strains;

DETAILED DESCRIPTION OF THE INVENTION

Figure 1:
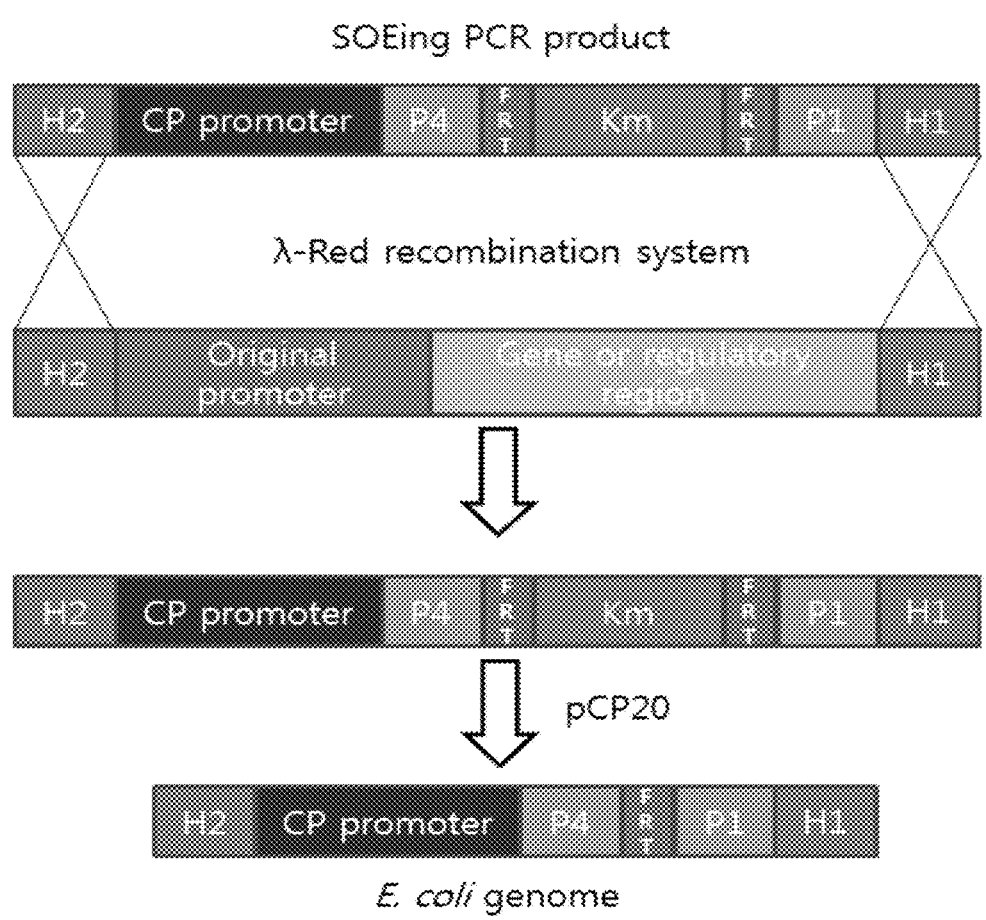
FIG. 1 is a schematic view of the replacement process of an inducible promoter (endogenous promoter) on the chromosome of *E. coli* with the constitutive promoter CP by use of a λ-Red recombination system.
Figure 2:
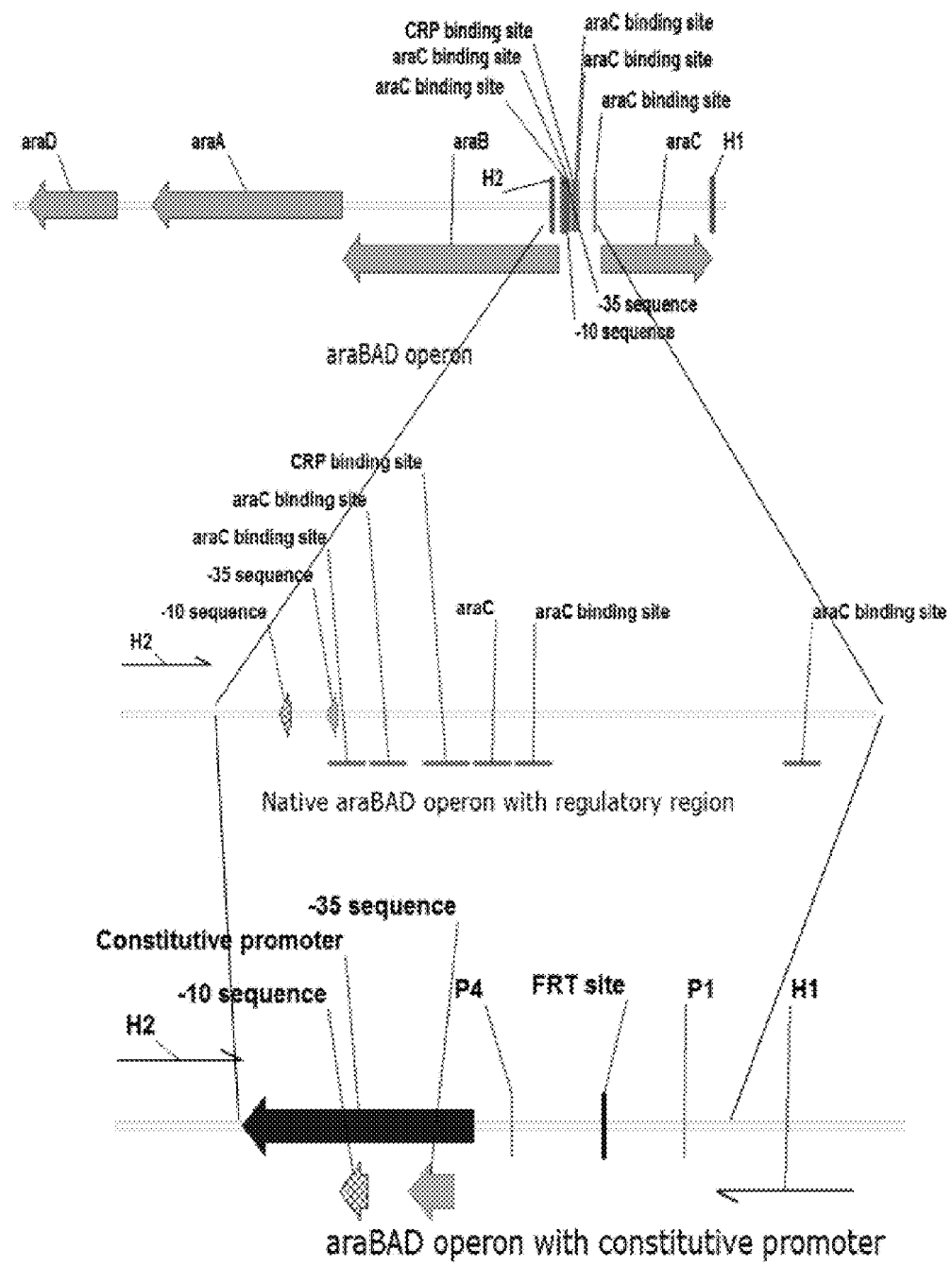
FIG. 2 illustrates a replacement process of the inducible promoter of araBAD operon with a constitutive promoter.

Hereinafter, the terms used herein are defined.

As used herein, the term "operon" refers to a functioning unit of genomic DNA containing a cluster of genes under the control of a single regulatory signal or promoter. Structures and functions of 'araBAD operon', 'araFGH operon', 'xylAB operon' and 'xylFGH operon' used in the present invention are known in the art.

The term "promoter," as used herein, refers to a region of DNA that helps transcription of a particular gene. The term "inducible promoter," as used herein, refers to a promoter; the activity of which is induced by the presence or absence of a particular factor. The term "constitutive promoter" refers to an unregulated promoter that allows for the continual expression of a relevant gene. The inducible promoters of araBAD operon, araFGH operon, araE gene, xylAB operon, and xylFGH operon are known in the art.

The present invention provides a method for preparing a mutant *E. coli* capable of simultaneously utilizing glucose and xylose from the wild-type, comprising: (1) replacing inducible promoters of araBAD operon, araFGH operon, araE gene, xylAB operon, and xylFGH operon of a wild-type *E. coli* with respective constitutive promoters; and (2) growing the promoter-replaced *E. coli* in a xylose minimal medium or an arabinose and xylose minimal medium for 10 days or longer.

It is difficult to use a wild-type *E. coli* in industry to produce various chemicals, for example, amino acids, biofuels, biopolymers, bioalcohols, etc., from a biomass because a wild-type *E. coli* cannot simultaneously utilize glucose and xylose due to carbon catabolite repression (CCR). In contrast, the mutant *E. coli* of the present invention significantly reduces the time taken by biochemical processes for producing the chemicals, with concomitant increase in fermentation efficiency, yield and productivity, and decrease in the cost of process operation.

These characteristics can be achieved by a genetic engineering method of replacing inducible promoters of araBAD operon, araFGH operon, araE gene, xylAB operon and xylFGH operon on the chromosome of *E. coli* with respective constitutive promoters; in combination with the evolutionary adaptation of growing the strain in a xylose minimal medium or an arabinose and xylose minimal medium.

In the present invention, step 1 is set forth to substitute inducible promoters of araBAD operon, araFGH operon, araE gene, xylAB operon, and xylFGH operon of a wild-type *E. coli* with respective constitutive promoters.

Of the araBAD operon, araB codes for L-ribulokinase, araA for L-arabinose isomerase, and araD for L-ribulose-5-phosphatase 4-epimerase. By araF, araG, and araH, arabinose ABC transporter subunits are respectively encoded, and araE accounts for arabinose/hydrogen ion symporter. The inducible promoter for araBAD operon has the nucleotide sequence of SEQ ID NO: 1. The inducible promoters of araFGH operon and araE have the nucleotide sequences of SEQ ID NOS: 2 and 3, respectively.

In this step, the procedure of replacing inducible promoters of araBAD operon, araFGH operon and araE gene with respective, well-known constitutive promoters may be performed by splice overlap extension (SOE) PCR using a λ-Red recombination system as illustrated in FIGS. 1 to 4, but an alternative method known in the art may be employed. So long as it is known to allow for the constitutive transcription of a particular gene, any constitutive promoter may be used in the present invention. Preference is given to CP25 promoter, having the nucleotide sequence of SEQ ID NO: 6 or to CP6 promoter, having the nucleotide sequence of SEQ ID NO: 7. According to a report [Jensen, P. R. and K. Hammer (1998). "The sequence of spacers between the consensus sequences modulates the strength of prokaryotic promoters." Applied and Environmental Microbiology 64(1): 82-87], CP25 promoter is known to be the strongest in constitutive activity, and CP6 promoter ranks second. In one embodiment of the present invention, inducible promoters of araBAD operon and araE gene are replaced by CP25 promoter while the inducible promoter for araFGH operon is replaced by CP6 promoter.

Figure 5:
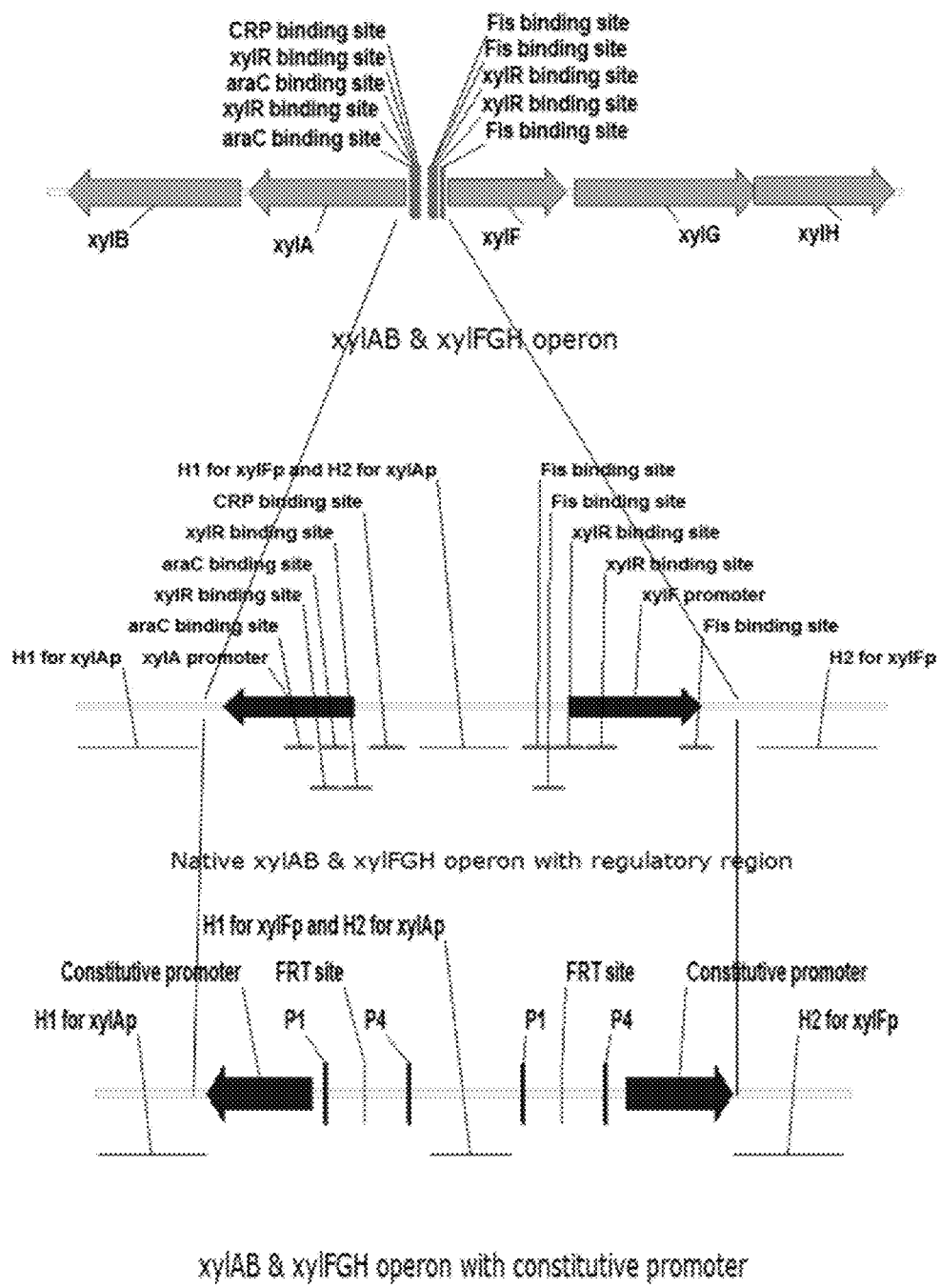
FIG. 5 illustrates a replacement process of the inducible promoters of xylAB operon and xylFGH operon with constitutive promoters.

Likewise, in this step, the procedure of replacing inducible promoters of xylAB operon and xylFGH operon with respective, well-known constitutive promoters may be performed by splice overlap extension (SOE) PCR using a λ-Red recombination system, as illustrated in FIG. 5, but may be also carried by an alternative method known in the art.

Of the xylAB operon, xylA codes for D-xylose isomerase while xylB encodes xylulokinase. By xylF, xylG, and xylH in xylFGH operon, D-xylose ABC transporter subunits are encoded, respectively. The inducible promoters of xylAB operon and xylFGH operon have the nucleotide sequences of SEQ ID NOS: 4 and 5, respectively.

Any known promoter that can constitutively transcribe a particular gene may be employed in the present invention. Preference is given to CP25 promoter, having the nucleotide sequence of SEQ ID NO: 6; or to CP6 promoter, having the nucleotide sequence of SEQ ID NO: 7. In one embodiment of the present invention, the inducible promoter for xylAB operon is replaced by CP25 promoter while the inducible promoter for xylFGH operon is replaced by CP6 promoter.

The *E. coli* strain obtained by the mutation procedures acquires the phenotype of simultaneously utilizing glucose and xylose as the araBAD operon, the araFGH operon, the araE gene, the xylAB operon and the xylFGH operon are activated under the control of the constitutive promoters instead of the inducible promoters.

In the present invention, step 2 is set forth to subject the *E. coli* mutated in step 1 to evolutionary adaptation by growing the E. coli in a xylose minimal medium or an arabinose and xylose minimal medium for 10 days or longer. Herein, the term 'xylose minimal medium' refers to a medium containing xylose as a sole carbon source. Examples of the xylose minimal medium include, but are not limited to, M9-minimal medium containing xylose 4 g/L, disodium hydrogen phosphate 6.78 g/L, potassium phosphate monobasic 3.0 g/L, sodium chloride 0.5 g/L, ammonium chloride 1.0 g/L, magnesium sulfate 2 mM, and calcium chloride 0.1 mM. The term 'arabinose and xylose minimal medium' refers to a medium containing no carbon sources other than arabinose and xylose. Examples of the medium include M9-minimal medium containing arabinose 2 g/L, xylose 2 g/L, disodium hydrogen phosphate 6.78 g/L, potassium phosphate monobasic 3.0 g/L, sodium chloride 0.5 g/L, ammonium chloride 1.0 g/L, magnesium sulfate 2 mM and calcium chloride 0.1 mM, but are not limited thereto. Further, the growth period is a minimal duration which may affect the utility of glucose and xylose, and the strain may be grown or adapted for 10 days or longer, 20 days or longer, 30 days or longer, 40 days or longer, or 50 days or longer.

The present invention also provides a mutant E. coli strain, capable of simultaneously utilizing glucose and xylose, prepared by replacing inducible promoters of araBAD operon, araFGH operon, araE gene, xylAB operon, and xylFGH operon of a wild-type E. coli with respective constitutive promoters, and growing the promoter-replaced E. coli in a xylose minimal medium or an arabinose and xylose minimal medium for 10 days or longer.

E. coli and constitutive promoters which are used for the preparation of the E. coli strain of the present invention are as described in the preparation method.

Furthermore, the present invention provides a method for producing a biofuel, a biologically active ingredient, a medicinal material, or a chemical substance for the chemical industry from a biomass by using the mutant E. coli according to the present invention. The biomass may be preferably a cellulosic biomass, and more preferably a lignocellulosic biomass. Methods for producing a biofuel from a biomass are widely known in the art. The present invention is characterized by using the mutant E. coli strain according to the present invention in an enzymatic saccharification process and a fermentation process. In one embodiment of the present invention, the saccharification process may be performed with the mutant E. coli strain according to the present invention, instead of all or some of the enzymes. In another embodiment of the present invention, the fermentation process may be performed with the mutant E. coli strain according to the present invention. Further, the mutant E. coli strain according to the present invention may be used in simultaneous saccharification fermentation (SSF) that is designed to simultaneously perform an enzymatic saccharification process and a fermentation process in one reactor.

Moreover, the mutant E. coli strain according to the present invention may be applied to the production of chemicals such as amino acids, biofuels, biopolymers, bioalcohols, recombinant proteins, etc. from a biomass.

A better understanding of the present invention may be obtained through the following examples which are set forth to illustrate, but are not to be construed as limiting the present invention.

Example 1

Preparation of Mutant E. coli by Promoter Replacement and Evolutionary Adaptation A mutant E. coli was prepared by replacing inducible promoters of araBAD operon, araFGH operon, araE gene, xylAB operon and xylFGH operon of a wild-type E. coli with respective constitutive promoters in the manner described below.

<1-1> Replacement of Inducible Promoters of araBAD Operon, araFGH Operon and araE Gene with Constitutive Promoters Using the λ-Red recombination system described by Datta et al. (Datta, S., N. Costantino, et al. (2006). "A set of recombineering plasmids for gram-negative bacteria." Gene 379(0): 109-115), the inducible promoter (SEQ ID NO: 1) of araBAD on the chromosome of E. coli MG1655 was replaced with the constitutive CP25 promoter (SEQ ID NO: 6) (refer to FIG. 1).

Briefly, two overlapping fragments for promoter replacement were amplified via Splice Overlap Extension (SOE) PCR to attach the CP25 promoter to a kanamycin cassette, as described in the document [Datta, S., N. Costantino, et al. (2006). "A set of recombineering plasmids for gram-negative bacteria." Gene 379(0): 109-115; Datsenko K A et al., Proceedings of the National Academy of Sciences of the United States of America, 97(12), 6640-6645, 2000; and Cherepanov, P P., W Wackernagel. (1995). Gene disruption in Escherichia coli: $Tc^R$ and $Km^R$ cassettes with the option of Flp-catalyzed excision of the antibiotic-resistance determinant. Gene 158(1): 9-14.]. Fragment 1 has the constitutive promoter CP25 carrying a primer sequence homologous to a downstream region of the araB promoter, and thus is configured to attach the constitutive promoter CP25 to a downstream region of the araB promoter using the three SOEing primers listed in Table 1. Fragment 2 contains a kanamycin cassette from pKD13 which starts with an overhang homologous to an upstream region of the araB promoter and terminates with a homologous sequence allowing for attachment to Fragment 1. After starting at 98° C. for 3 min, the SOE PCR was performed with 30 thermal cycles of 95° C. for 30 sec, 50–60° C. for 30 sec and 72° C. for 2 min. The process is schematically described in FIG. 2, and primers and plasmids used in the process are given in the Table 1.

TABLE 1

| Primer & Plasmid | Characteristic | Note |
|---|---|---|
| SOEing primer | 5'-CCCTATGCTACTCCGTCAAGCCGTC AATTGTCTGATTCGTTACCAAGTGTAGG CTGGAGCTGCTTCG-3' | SEQ ID NO: 8 |
| | 5'-CATAGCTGTTTCCTGTGTGAACAGT ACTATGTGATTATACCAGCCCCCTCACT ACATGTCAAGAATAAACTGCCAAAGATT CCGGGGATCCGTCGACC-3' | SEQ ID NO: 9 |
| | 5'-TCGCACAGAATCACTGCCAAAATCG AGGCCAATTGCAATCGCCATAGCTGTTT CCTGTGTGAAC-3' | SEQ ID NO: 10 |
| Sequencing primer | 5'-AACTGGTTATTCGGGGCATC-3' | SEQ ID NO: 11 |
| | 5'-AGGCGTGCCAGAAACTTAAC-3' | SEQ ID NO: 12 |
| pSIM5 | λ-Red recombinase expression plasmid; temperature-sensitive replication | Datta et al 2006 |
| pKD13 | Template plasmid for gene disruption. The resistance gene is flanked by FRT sites. oriR6K-gamma origin requiring the pir + E. coli. | Datsenko and Wanner 2000 |
| pCP20 | Carrying Flp recombinase of yeast, and chloramphenicol- or ampicillin-resistant gene; temperature-sensitive replication | Cherepanov and Wackernagel 1995 |

Figure 3:
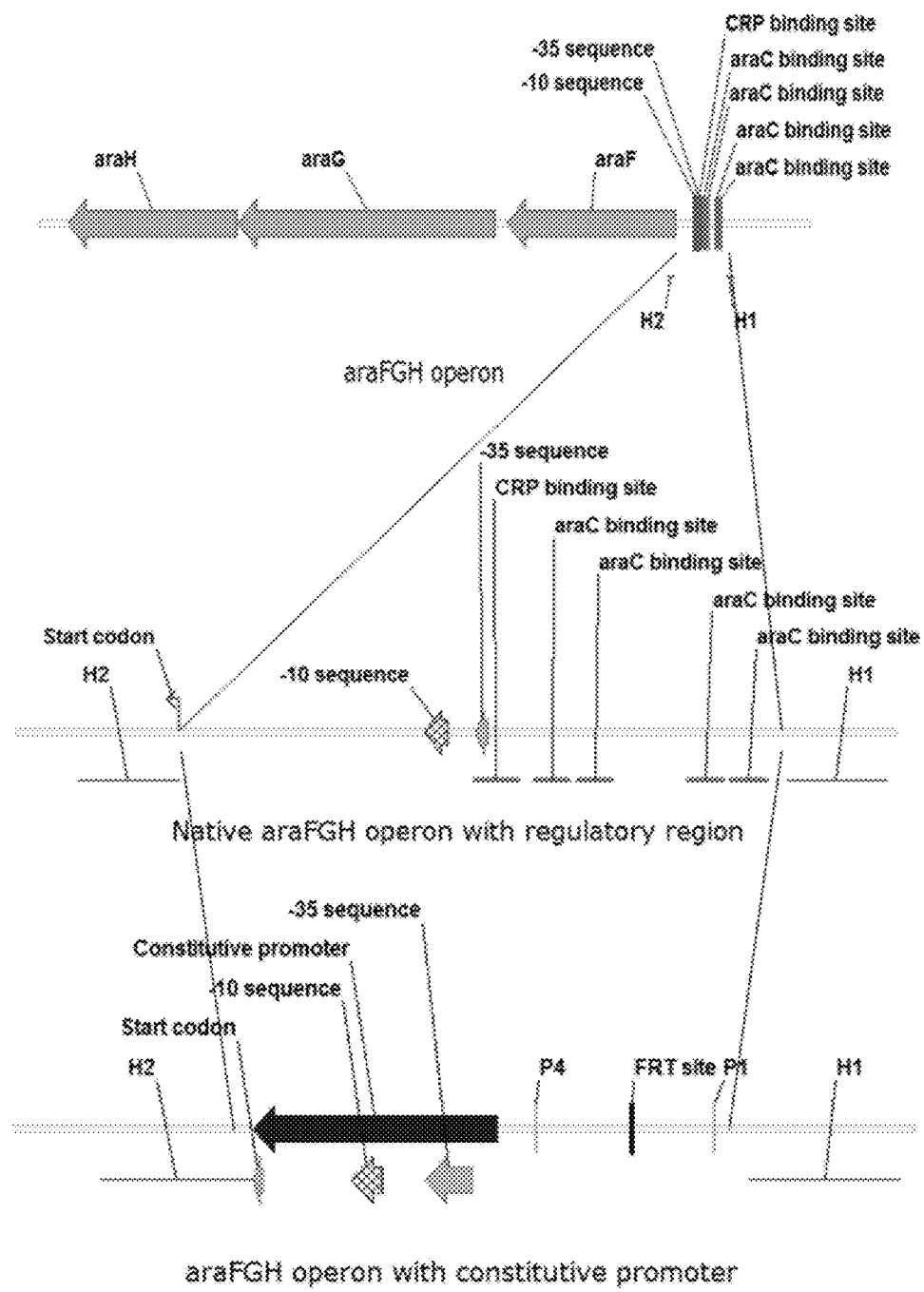
FIG. 3 illustrates a replacement process of the inducible promoter of araFGH operon with a constitutive promoter.

On the other hand, the inducible promoter of araFGH operon was replaced with CP6 promoter (SEQ ID NO: 7) in the same manner as described above. The procedure is schematically illustrated in FIG. 3, and SOEing primers and plasmids used in this procedure are given in Table 2, below.

TABLE 2

| Primer & Plasmid | Characteristic | Note |
|---|---|---|
| SOEing primer | 5'-GGTAATGCGGCCTATTGACTGGTTAA AAAGAAGACATCCCGCATGGGTAGTGTAG GCTGGAGCTGCTTCG-3' | SEQ ID NO: 13 |
| | 5'-CATAGCTGTTTCCTGTGTGAACAGTA CTCAGTTATTATATCATCCGGAAATATCT GTGTCAAGAATAAACTCCCACATGATTCC GGGGATCCGTCGACC-3' | SEQ ID NO: 14 |
| | 5'-GACATAACGGCTGCCAGACCAATGGC TGCCAGGGCTTTAGTAAATTTGTGCATAG CTGTTTCCTGTGTGAACAGTACT-3' | SEQ ID NO: 15 |
| Sequencing primer | 5'-GCTCTCATTATACGTGTTCTG-3' | SEQ ID NO: 16 |
| | 5'-CCTCAAACCCTAAATCCTTCC-3' | SEQ ID NO: 17 |
| pSIM5 | λ-Red recombinase expression plasmid; temperature-sensitive replication | Datta et al 2006 |
| pKD13 | Template plasmid for gene disruption. The resistance gene is flanked by FRT sites. oriR6K-gamma origin requiring the pir + E. coli. | Datsenko and Wanner 2000 |
| pCP20 | Carrying Flp recombinase of yeast, and chloramphenicol- or ampicillin-resistant gene; temperature-sensitive replication | Cherepanov and Wackernagel 1995 |

The inducible promoter of araE gene was replaced by CP6 promoter (SEQ ID NO: 7) in the same manner as described above.

Figure 4:
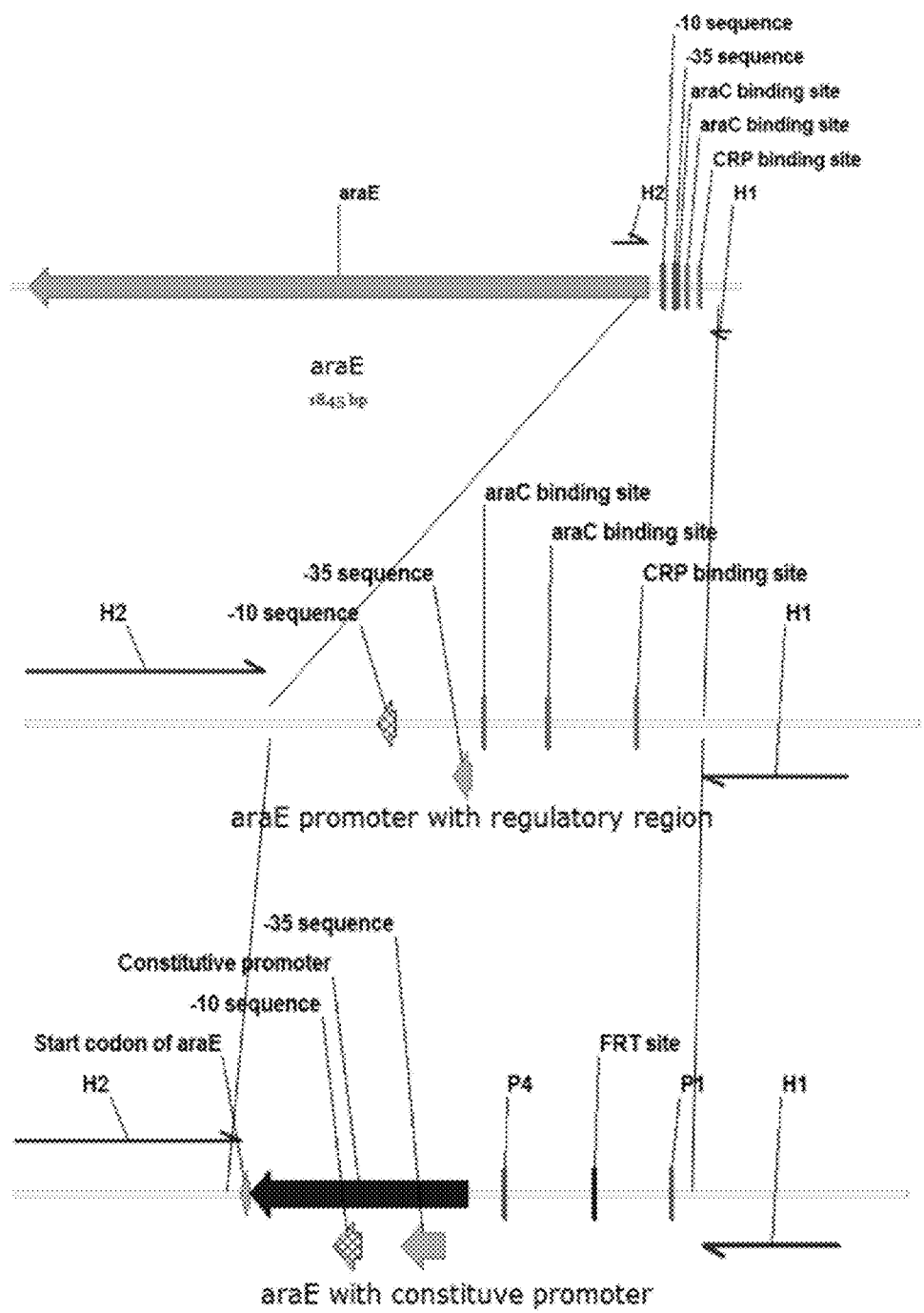
FIG. 4 illustrates a replacement process of the inducible promoter of araE gene with a constitutive promoter.

The procedure is briefly illustrated in FIG. 4, and SOEing primers and plasmids used in this procedure are given in Table 3, below.

TABLE 3

| Primer & Plasmid | Characteristic | Note |
|---|---|---|
| SOEing primer | 5'-TATCTGCTGTAAAATTAGGTGGTTA ATAATAATCTCAATAATTCAACGTGTAG GCTGGAGCTGCTTCG-3' | SEQ ID NO: 18 |
| | 5'-CATAGCTGTTTCCTGTGTGAACAGT ACTCAGTTATTATATCATCCGGAAATAT CTGTGTCAAGAATAAACTCCCACATGAT TCCGGGGATCCGTCGACC-3' | SEQ ID NO: 19 |
| | 5'-CCCGCAAAGAACGTGGCGTTAAAGC AGATTCCGTATTGATAGTAACCATAGCT GTTTCCTGTGTGAACAGTACT-3' | SEQ ID NO: 20 |
| Sequencing primer | 5'-CATTCTTCTTACTTTTATG-3' | SEQ ID NO: 21 |
| | 5'-CTGGTCAGCACAAAGTGATC-3' | SEQ ID NO: 22 |
| pSIM5 | λ-Red recombinase expression plasmid; temperature-sensitive replication | Datta et al 2006 |

TABLE 3-continued

| Primer & Plasmid | Characteristic | Note |
|---|---|---|
| pKD13 | Template plasmid for gene disruption. The resistance gene is flanked by FRT sites. oriR6K-gamma origin requiring the pir + E. coli. | Datsenko and Wanner 2000 |
| pCP20 | Carrying Flp recombinase of yeast, and chloramphenicol- or ampicillin-resistant gene; temperature-sensitive replication | Cherepanov and Wackernagel 1995 |

<1-2> Replacement of Inducible Promoters of xylAB Operon and xylFGH Operon with Respective Constitutive Promoters The inducible promoter (SEQ ID NO: 4) of the xylAB operon on the chromosome of *E. coli* MG1655 was replaced with the synthetic, constitutive CP25 promoter (SEQ ID NO: 6) in the same manner as in Example <1-1> (refer to FIG. 1).

Briefly, with reference to documents [Datta, S., N. Costantino, et al. (2006). "A set of recombineering plasmids for gram-negative bacteria." Gene 379(0): 109-115; Datsenko K A et al., Proceedings of the National Academy of Sciences of the United States of America, 97(12), 6640-6645, 2000; and Cherepanov, P P., W Wackernagel. (1995). "Gene disruption in *Escherichia coli*: Tc$^R$ and Km$^R$ cassettes with the option of Flp-catalyzed excision of the antibiotic-resistance determinant. Gene 158(1):9-14.], two overlapping fragments for promoter replacement were amplified via Splice Overlap Extension (SOE) PCR to attach the CP25 promoter to a kanamycin cassette. Fragment 1 has the constitutive promoter CP25 carrying a primer sequence homologous to a downstream region of the xylA promoter, and thus is configured to join the constitutive promoter CP25 to a downstream region of the xylA promoter using the two SOEing primers listed in Table 4. Fragment 2 contains a kanamycin cassette from pKD13 which starts with an overhang homologous to an upstream region of the xylA promoter and terminates with a homologous sequence allowing for joining to Fragment 1. After starting at 98° C. for 3 min, the SOE PCR was performed with 30 thermal cycles of 95° C. for 30 sec, 50~60° C. for 30 sec and 72° C. for 2 min. The process is schematically described in FIG. 5, and primers and plasmids used in the process are given in the Table 4.

TABLE 4

| primer & plasmid | Characteristic | Note |
|---|---|---|
| SOEing primer | 5'-CGAAGCAGCTCCAGCCTACACCTTT GGCAGTTTATTCTTGACATGTAGTGAGG GGGCTGGTATAATCACATAGTACTGTTC ACACAGGAAACAGCTATGCAAGCCTATT TTGACCAGCTCGATCGCGTTCGTTATGA AGGCTCA-3' | SEQ ID NO: 23 |
| | 5'-TTGTTGCGCAATTGTACTTATTGCA TTTTTCTCTTCGAGGAATTACCCAGTTT CATCAATTCCGGGGATCCGTCGACC-3' | SEQ ID NO: 24 |
| Sequencing primer | 5'-AACTCAAATGCGACATCTGC-3' | SEQ ID NO: 25 |
| | 5'-ATGCCTTCTTGTTTGGCTTC-3' | SEQ ID NO: 26 |

TABLE 4-continued

| primer & plasmid | Characteristic | Note |
|---|---|---|
| pSIM5 | λ-Red recombinase expression plasmid; temperature-sensitive replication | Datta et al 2006 |
| pKD13 | Template plasmid for gene disruption. The resistance gene is flanked by FRT sites. oriR6K-gamma origin requiring the pir + E. coli. | Datsenko and Wanner 2000 |
| pCP20 | Carrying Flp recombinase of yeast, and chloramphenicol- or ampicillin- resistant gene; temperature-sensitive replication | Cherepanov and Wackernagel 1995 |

On the other hand, the inducible promoter (SEQ ID NO: 5) of xylFGH operon was replaced with CP6 promoter (SEQ ID NO: 7) in the same manner as described above.

The procedure is schematically illustrated in FIG. 5, and SOEing primers and plasmids used in this procedure are given in Table 5, below.

TABLE 5

| primer & plasmid | Characteristic | Note |
|---|---|---|
| SOEing primer | 5'-TGATGAAACTGGGTAATTCCTCGAA GAGAAAAATGCAATAAGTACAATTGCGC AACAAGTGTAGGCTGGAGCTGCTTCG-3' | SEQ ID NO: 27 |
| | 5'-CATAGCTGTTTCCTGTGTGAACAGT ACTCAGTTATTATATCATCCGGAAATAT CTGTGTCAAGAATAAACTCCCACATGAT TCCGGGGATCCGTCGACC-3' | SEQ ID NO: 28 |
| | 5'-GACTTCTTTGGCGTGTGCAGCAACG TTGGTAAGCAGGAGTGAGGTGCAAAGGG TGAGTAGAATGTTCTTTATTTTCATAGC TGTTTCCTGTGTGAAC-3' | SEQ ID NO: 29 |
| Sequencing primer | 5'-AACTCAAATGCGACATCTGC-3' | SEQ ID NO: 30 |
| | 5'-ATGCCTTCTTGTTTGGCTTC-3' | SEQ ID NO: 31 |
| pSIM5 | λ-Red recombinase expression plasmid; temperature-sensitive replication | Datta et al 2006 |
| pKD13 | Template plasmid for gene disruption. The resistance gene is flanked by FRT sites. oriR6K-gamma origin requiring the pir + E. coli. | Datsenko and Wanner 2000 |
| pCP20 | Carrying Flp recombinase of yeast, and chloramphenicol- or ampicillin- resistant gene; temperature-sensitive replication | Cherepanov and Wackernagel 1995 |

<1-3> Deletion of Kanamycin-Resistant Gene

To perform the consecutive transformation of the PCR products respectively obtained in Examples <1-1> and <1-2>, the deletion of the kanamycin-resistant gene inserted in a previous step was required. In this regard, E. coli was transformed with the plasmid pCP20 (Cherepanov, P. P. and W. Wackernagel (1995). "Gene disruption in Escherichia coli: TcR and KmR cassettes with the option of Flp-catalyzed excision of the antibiotic-resistance determinant." Gene 158 (1): 9-14), and then streaked on an antibiotic-free LB agar plate containing ampicillin. The strains thus obtained were streaked on antibiotic-free LB agar plates, followed by induction at 42° C. overnight. The strains which underwent these processes were again streaked on antibiotic-free LB agar plates, and then subjected to induction at 42° C. for one day. Thereafter, the colonies were inoculated into kanamycin LB agar plates, ampicillin LB agar plates, and antibiotic-free LB agar plates, followed by incubation at 42° C. overnight. Final selection was made of the strains which grew only on the antibiotic-free agar plates.

The strain which was prepared from a wild-type E. coli by replacing the inducible promoters of araBAD operon, araFGH operon and araE gene, and the promoters of xylAB operon and xylFGH operon with constitutive promoters was designated "AXcp."

<1-4> Evolutionary Adaptation of Mutant E. coli

The strain prepared in Example <1-3> was grown at 37° C. for 50 days in a xylose minimal medium (M9-minimal medium supplemented with xylose 4 g/L, disodium hydrogen phosphate 6.78 g/L, potassium phosphate monobasic 3.0 g/L, sodium chloride 0.5 g/L, ammonium chloride 1.0 g/L, magnesium sulfate 2 mM, and calcium chloride 0.1 mM) while stirring at 200 rpm. The cells were transferred to a fresh medium whenever the culture medium reached an $OD_{600}$ of 1.0.

The strain which underwent the evolutionary adaptation to a xylose minimal medium after the replacement of the inducible promoters of araBAD operon, araFGH operon and araE and the inducible promoters of xylAB operon and xylFGH operon with constitutive promoters was designated "AXcpX50".

Example 2

Preparation of Mutant E. coli by Promoter Replacement and Evolutionary Adaptation in Arabinose and Xylose Minimal Medium A mutant E. coli strain was prepared in the same manner as in Example 1 with the exception that the strain established in Example <1-3> was cultured for 50 days in an arabinose and xylose minimal medium (M9-minimal medium supplemented with arabinose 2 g/L, xylose 2 g/L, bisodium hydrogen phosphate 6.78 g/L, potassium phosphate monobasic 3.0 g/L, sodium chloride 0.5 g/L, ammonium chloride 1.0 g/L, magnesium sulfate 2 mM and calcium chloride 0.1 mM) instead of the xylose minimal medium.

The strain which underwent the evolutionary adaptation to an arabinose and xylose minimal medium after the replacement of the inducible promoters of araBAD operon, araFGH operon and araE and the inducible promoters of xylAB operon and xylFGH operon with constitutive promoters was designated "AXcpAX50".

Example 3

Preparation of ptsG-Knockout Strain

<3-1> Preparation of ptsG-Knockout, Wild-Type E. coli

To examine the molecular mechanism of the mutant strain (AXcpAX50) for CCR elimination, ptsG gene disruption was performed within the chromosome. As previously reported (Nichols et al., Appl. Microbiol. Biotechnol., 2001, 56: 120-125), a strain mutated in ptsG encoding the glucose transporter $EIIBC^{Glc}$ is known to simultaneously utilize glucose and xylose. For use in elucidating that the molecular mechanism of the mutant E. coli strain is attributed to the new mutant factor, a wild-type *E. coli* MG1655 with ptsG deletion was prepared. The ptsG disruption was carried out by replacing a ptsG gene encoding sequence with a kanamycin-resistant gene in the same manner as described for the promoter replacement of Example 1, and then finally deleting the kanamycin-resistant gene in the same manner as in Example <1-3>. As such, ptsG-knockout *E. coli* MG1655 was designated "WTΔptsG."

<3-2> Preparation of ptsG-Knockout, AXcpAX50 Strain

A ptsG gene was deleted from the AXcpAX50 strain of Example 2 in the same manner as in Example <3-1>, and the resulting strain was designated "AXΔptsG".

Example 4

Preparation of Various Mutant *E. coli* Strains by Multiplex Automated Genome Engineering To screen various phenotypes of genes involved in the simultaneous utilization of glucose and xylose within the mutant *E. coli* strain of Examples 1 and 2, multiplex automated genomic engineering (MAGE) was carried out.

Briefly, using the plasmid pRED2 carrying a lamda recombinase gene, a lamda recombinase gene was inserted into the AXcp strain of Example 2 at the site of mutS gene responsible for DNA repair, as described previously [Wang, H. H. et al. (2009). "Programming cells by multiplex genome engineering and accelerated evolution." Nature 460: 894-898; Wang, H. H. et al. (2012). "Genome-scale promoter engineering by coselection MAGE." Nature methods 9: 591-593], to prepare an "AXcpM" strain, which was devoid of mutS gene. Meanwhile, MAGE primers listed in Table 6 were synthesized on the basis of 7 mutant gene sequences found in the mutant strains of Examples 1 and 2.

TABLE 6

| Primer | Sequence | Use | Note |
| --- | --- | --- | --- |
| MutS A1R | 5'-CTCTCATCCGCCAAAACA GCCCATAACCCATGAGTGCAA TAG-3' | Preparation of AXcpM | SEQ ID NO: 32 |
| Cm R | 5'-CCGTTTTCACCATGGGCA AATATTATACG-3' | | SEQ ID NO: 33 |
| MutS A5F | 5'-GTATAATCACATAGTACT GTTTTACACCAGGCTCTTCAA GCGATA-3' | Preparation of AXcpM | SEQ ID NO: 34 |
| pSIM5 UP | 5'-CAGTGCGTCCTGCTGATG TGC-3' | | SEQ ID NO: 35 |
| araF-F | 5'-GCTCTCATTATACGTGTT CTG-3' | MAGE | SEQ ID NO: 36 |
| araF-R | 5'-CCTCAAACCCTAAATCCT TCC-3' | | SEQ ID NO: 37 |
| xylA-F | 5'-AACTCAAATGCGACATCT GC-3' | MAGE | SEQ ID NO: 38 |
| xylA-R | 5'-ATGCCTTCTTGTTTGGCT TC-3' | | SEQ ID NO: 39 |
| araE SNP-F | 5'-GCTATAACTGAACGCTGT ATC-3' | MAGE | SEQ ID NO: 40 |
| araE SNP-R | 5'-CTGCTTTAACGCCACGTT CT-3' | | SEQ ID NO: 41 |
| ybjG-F | 5'-CCACGATTGCAGACGTTG AT-3' | MAGE | SEQ ID NO: 42 |
| ybjG-R | 5'-CGCCAGACTCGGCTCCGT GG-3' | | SEQ ID NO: 43 |
| thiC-F | 5'-TAAATGCGTTTTGAGTTG GG-3' | MAGE | SEQ ID NO: 44 |

TABLE 6-continued

| Primer | Sequence | Use | Note |
| --- | --- | --- | --- |
| thiC-R | 5'-ATGGATTACTACGATTCC AG-3' | | SEQ ID NO: 45 |
| pyrE-F | 5'-GGGCCAAACAGCAGATCG AAC-3' | MAGE | SEQ ID NO: 46 |
| pyrE-R | 5'-GTCGGAATTGTGAACGGC GA-3' | | SEQ ID NO: 47 |

Insertion into the AXcpM strain by use of each MAGE primer was repeated four times, followed by culturing on a M9-minimal medium containing xylose 4 g/L. A total of 28 colonies utilizing xylose were selected on the basis of size. The selected colonies were cultured at 30° C. for 2 days in a xylose minimal medium (M9-minimal medium supplemented with xylose 4 g/L, disodium hydrogen phosphate 6.78 g/L, potassium phosphate monobasic 3.0 g/L, sodium chloride 0.5 g/L, ammonium chloride 1.0 g/L, magnesium sulfate 2 mM, and calcium chloride 0.1 mM) while shaking at 200 rpm. Of them, the strains which were observed to improve in the utility of xylose were designated "AXcpM#1, AXcpM#4, AXcpM#9, AXcpM#14, AXcpM#15, AXcpM#22, AXcpM#24, AXcpM#26, and AXcpM#28", respectively, and individual DNA sequences corresponding to the genes were identified.

As such, the mutS-knockout strain from which various mutant strains can be induced was designated "AXcpM", and 9 mutant strains which were observed to improve in xylose utility in a minimal medium via MAGE were designated "AXcpM#1, AXcpM#4, AXcpM#9, AXcpM#14, AXcpM#15, AXcpM#22, AXcpM#24, AXcpM#26, and AXcpM#28," respectively.

Example 5

Preparation of Xylitol-Producing Strain from the Mutant *E. coli*

On the basis of the mutant strain simultaneously utilizing glucose/xylose (AXcpAX50) of Example 2, a strain capable of producing xylitol, a highly valuable compound, was prepared. A gene of xylose reductase (XR), an enzyme converting xylose to xylitol, was amplified from the chromosome of *Candida boidinii* (from the Korean Collection for Type Culture) in the presence of a pair of primers of SEQ ID NOS: 48 and 49 by PCR, and cloned to an IPTG-inducible pBbB6a plasmid containing an ampicillin-resistant gene (source Biobricks). The resulting recombinant plasmid was designated "pBbB6a-XR." pBbB6a-XR was transformed into a wild-type *E. coli* and the mutant strain of Example 2 which were then streaked on LB agar plates containing ampicillin to select transformants. The transformants carrying pBbB6a-XR, prepared from a wild-type *E. coli* MG1655 and the mutant strain of Example 2, were designated "WT-pXR" and "AX-pXR," respectively. Both of them were xylitol-producing strains capable of simultaneously utilizing glucose/xylose.

As described above, an IPTG inducible pBbB6a engineered to carry xylose reductase, an enzyme catalyzing the reduction of xylose to xylitol, was designated "pBbB6a-XR", and transformants carrying pBbB6a-XR, derived from a wild-type *E. coli* MG1655 and the mutant strain (AXcpAX50) of Example 2, were designated "WT-pXR" and "AX-pXR," respectively.

Test Example 1

Examination of Mutant E. coli Strains for Glucose and Xylose Utilization

The mutant E. coli strains prepared in Examples 1 and 2 were measured for utilization of glucose and xylose, as follows.

The experimental strains were separately cultured in 50 mL of a glucose M9-minimal medium (glucose 4 g/L) and 50 mL of a xylose M9-minimal medium (xylose 4 g/L). Every two hours, 1 mL of each of the media was withdrawn and centrifuged. The supernatant was recovered and sterilized at 80° C. for 1 hr. After further centrifugation, 200 µL of the supernatant was mixed with 800 µL of deionized water containing 50 µg/mL kanamycin, and the residual concentrations of glucose and xylose were measured using a Shimadzu HPLC station equipped with HPX-87P (Bio-Rad) column and refractive index detector (Shimadzu). HPLC-grade water was used as mobile phase at the flow rate of 0.6 mL/min. The oven temperature was set to 80° C. A standard curve was determined on the basis of different concentrations of glucose and xylose. All experiments were carried out in triplicate and data were expressed as a mean±standard deviation from three independent measurements.

Figure 6A:
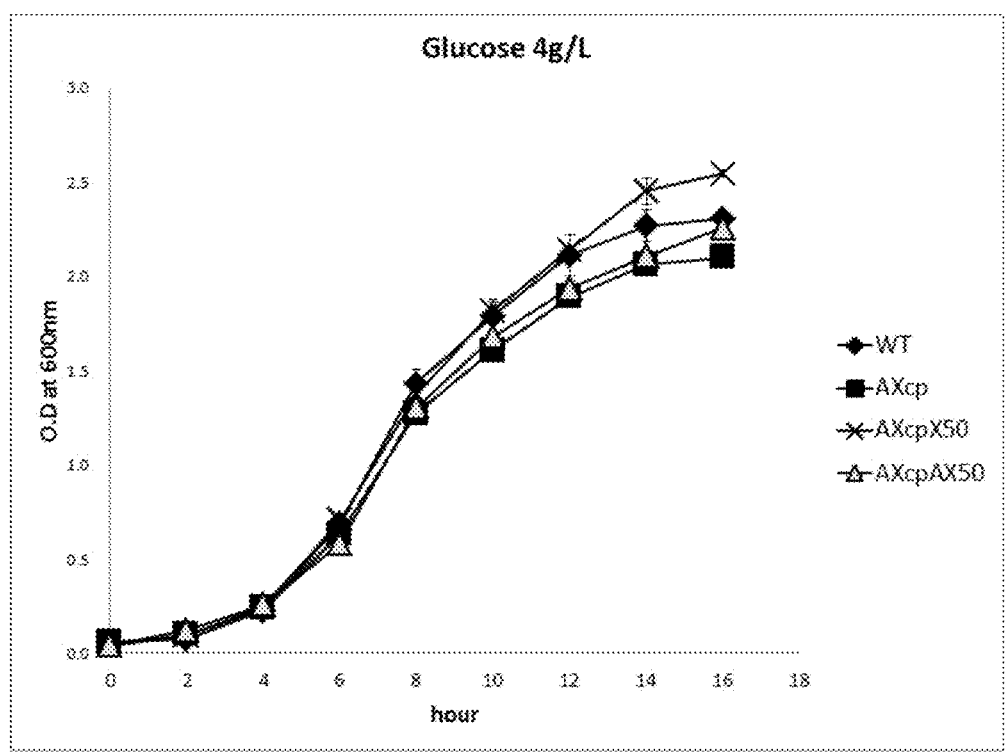
FIG. 6A depicts growth rates in a glucose minimal medium and FIG. 6B depicts growth rates in a xylose minimal medium, wherein diamonds (♦) stand for a wild-type *E. coli* (WT); rectangles (■) for the strain (AXcp) which had constitutive promoters replaced for inducible promoters of araBAD operon, araFGH operon and araE, and for inducible promoters of xylAB operon and xylFGH operon, but was not subjected to evolutionary adaptation; X for the strain (AXcpX50) of Example 1 which had constitutive promoters replaced for inducible promoters of araBAD operon, araFGH operon and araE, and for inducible promoters of xylAB operon and xylFGH operon and then was subjected to evolutionary adaptation in a xylose minimal medium; and triangles (Δ) for the strain (AXcpAX50) of Example 2 which had constitutive promoters replaced for inducible promoters of araBAD operon, araFGH operon and araE, and for inducible promoters of xylAB operon and xylFGH operon and then was subjected to evolutionary adaptation in an arabinose and xylose minimal medium.
Figure 6B:
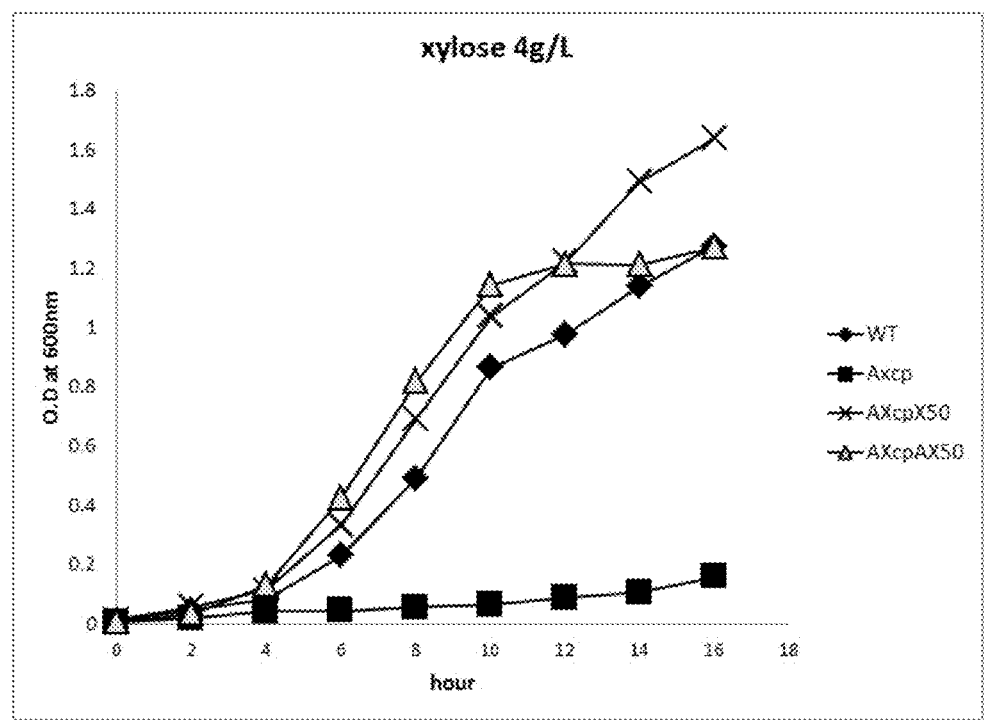
Figure 7A:
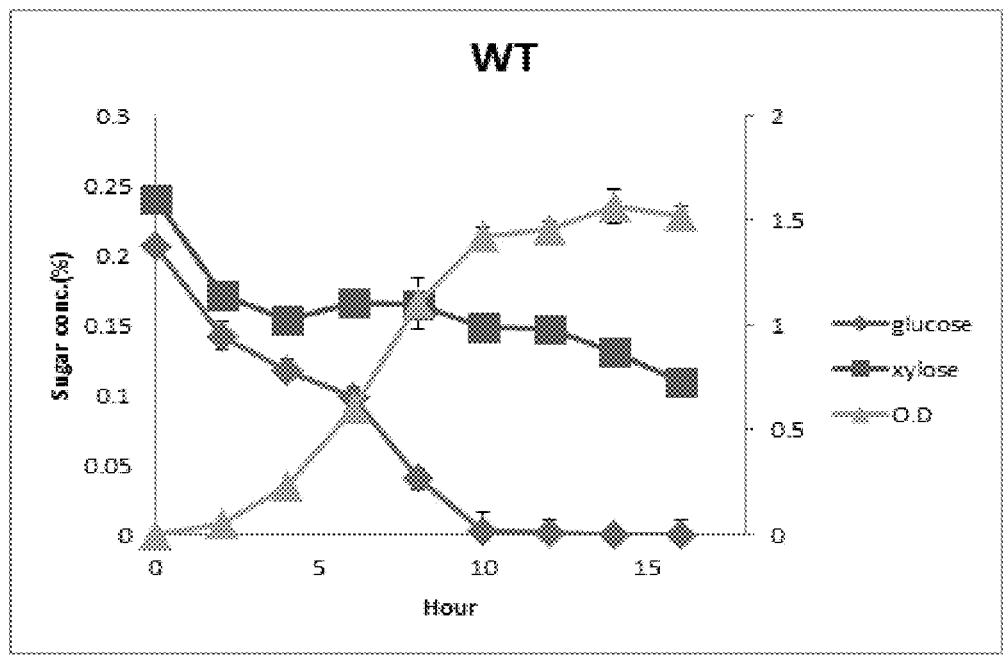
FIG. 7A depicts residual concentrations of glucose (♦) and xylose (■), and growth rates of a wild-type *E. coli* (WT)
Figure 7B:
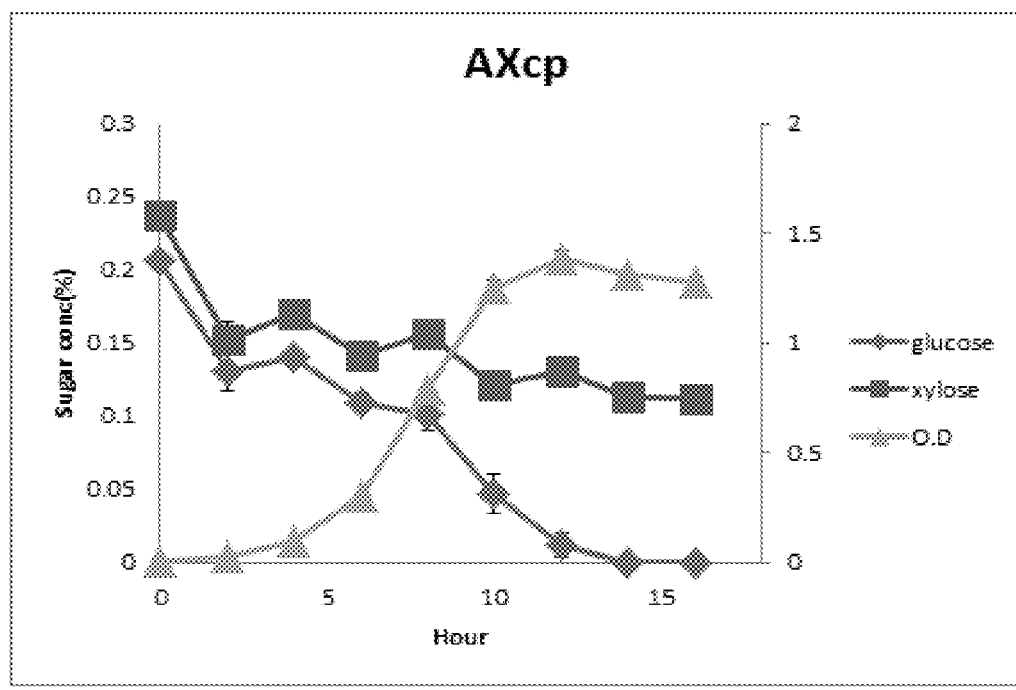
FIG. 7B depicts residual concentrations of glucose (♦) and xylose (■), and growth rates of the strain (AXcp) which had constitutive promoters replaced for inducible promoters of araBAD operon, araFGH operon and araE, and for inducible promoters of xylAB operon and xylFGH operon, but was not subjected to evolutionary adaptation.
Figure 7C:
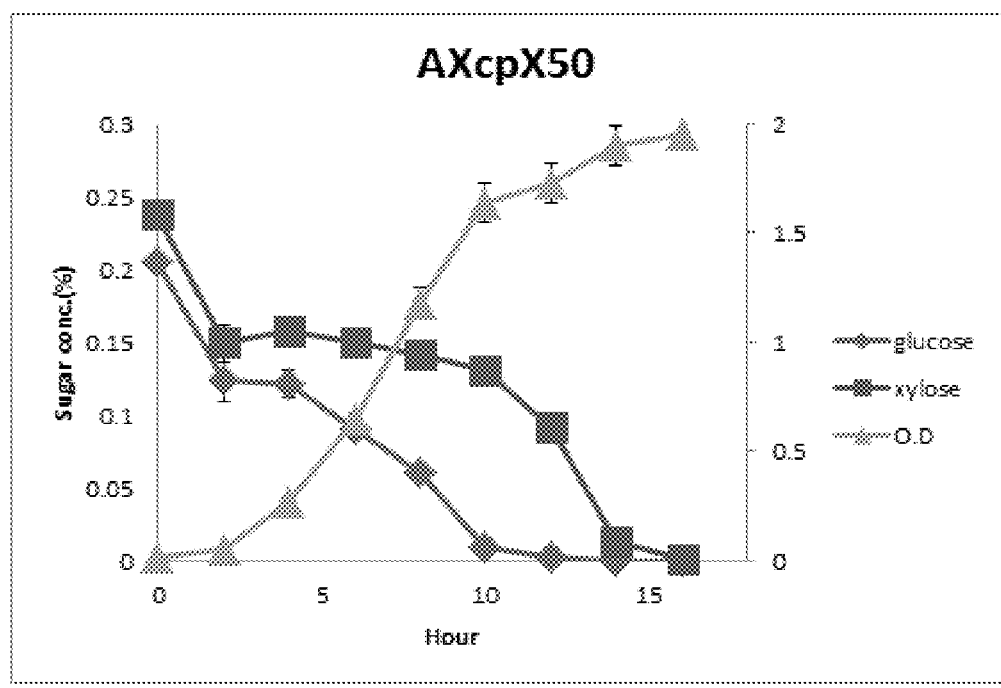
FIG. 7C depicts residual concentrations of glucose (♦) and xylose (■), and growth rates of the strain (AXcpX50) of Example 1 which had constitutive promoters replaced for inducible promoters of araBAD operon, araFGH operon and araE, and for inducible promoters of xylAB operon and xylFGH operon and then was subjected to evolutionary adaptation in a xylose minimal medium.
Figure 7D:
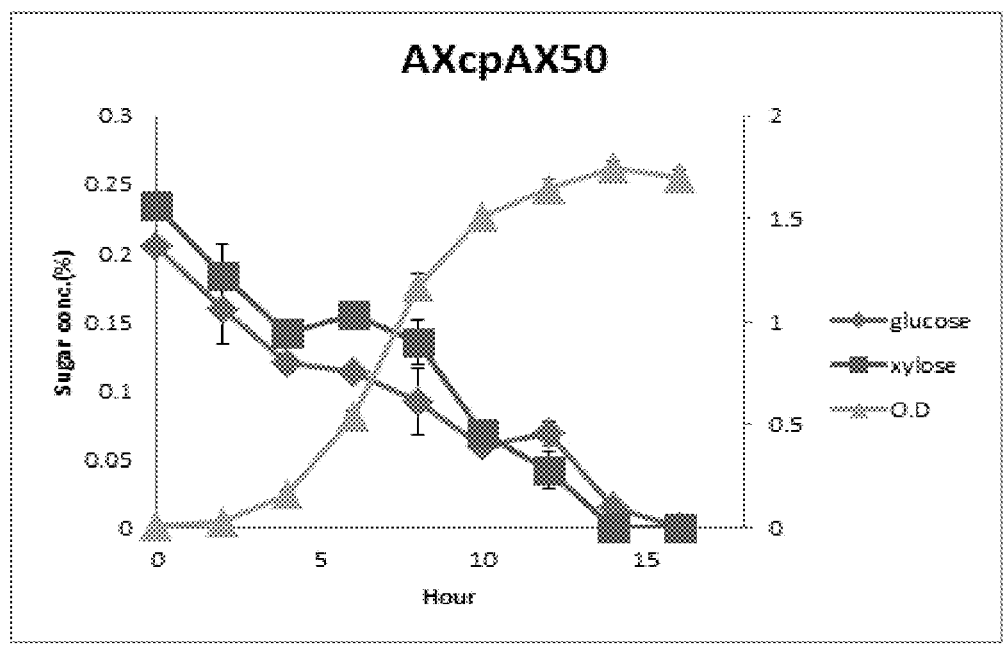
FIG. 7D depicts residual concentrations of glucose (♦) and xylose (■), and growth rates of the strain (AXcpAX50) of Example 2 which had constitutive promoters replaced for inducible promoters of araBAD operon, araFGH operon and araE, and for inducible promoters of xylAB operon and xylFGH operon and then was subjected to evolutionary adaptation in an arabinose and xylose minimal medium (D), each

The results are given in FIGS. 6A and 6B. FIGS. 6A and 6B depict growth rates in a glucose minimal medium (A) and in a xylose minimal medium (B) wherein diamonds (♦) stand for a wild-type E. coli (WT); rectangles (■) for the strain (AXcp) which had constitutive promoters replaced for inducible promoters of araBAD operon, araFGH operon and araE, and for inducible promoters of xylAB operon and xylFGH operon, but was not subjected to evolutionary adaptation; X for the strain (AXcpX50) of Example 1 which had constitutive promoters replaced for inducible promoters of araBAD operon, araFGH operon and araE, and for inducible promoters of xylAB operon and xylFGH operon and then was subjected to evolutionary adaptation in a xylose minimal medium; and triangles (Δ) for the strain (AXcpAX50) of Example 2 which had constitutive promoters replaced for inducible promoters of araBAD operon, araFGH operon and araE, and for inducible promoters of xylAB operon and xylFGH operon and then was subjected to evolutionary adaptation in an arabinose and xylose minimal medium.

As can be seen from the data, higher growth rates were observed in the strain (AXcpX50) of Example 1 which had constitutive promoters replaced for inducible promoters of araBAD operon, araFGH operon and araE, and for inducible promoters of xylAB operon and xylFGH operon and then was subjected to evolutionary adaptation in a xylose minimal medium, and the strain (AXcpAX50) of Example 2 which had constitutive promoters replaced for inducible promoters of araBAD operon, araFGH operon and araE, and for inducible promoters of xylAB operon and xylFGH operon and then was subjected to evolutionary adaptation in an arabinose and xylose minimal medium, compared to the wild-type E. coli.

The results show that the constitutive expression of araBAD operon, araFGH operon, araE gene, xylAB operon and xylFGH operon in combination with the evolutionary adaptation can increase xylose utilization.

Test Example 2

Examination of Mutant E. coli for Simultaneous Glucose and Xylose Utilization The mutant E. coli strains prepared in Examples 1 and 2 were measured for simultaneous utilization of glucose and xylose, as follows.

The experimental strains were seeded in 50 mL of an M9-minimal medium containing 2 g/L glucose and 2 g/L xylose. Every two hours, 1 mL of the medium was withdrawn and centrifuged. The supernatant was recovered and sterilized at 80° C. for 1 hr. After further centrifugation, 200 µL of the supernatant was mixed with 800 µL of deionized water containing 50 µg/mL kanamycin, and the residual concentrations of glucose and xylose were measured using a Shimadzu HPLC station equipped with HPX-87P (Bio-Rad) column and refractive index detector (Shimadzu). HPLC-grade water was used as mobile phase at the flow rate of 0.6 mL/min. The oven temperature was maintained at 80° C. A standard curve was determined on the basis of different concentrations of glucose and xylose. All experiments were carried out in triplicate and data were expressed as a mean±standard deviation from three independent measurements.

Results are given in FIGS. 7A to 7D. FIG. 7 depicts residual sugar concentrations and growth rates of a wild-type E. coli (WT) (A), the strain (AXcp) which had constitutive promoters replaced for inducible promoters of araBAD operon, araFGH operon and araE, and for inducible promoters of xylAB operon and xylFGH operon, but was not subjected to evolutionary adaptation (B), the strain (AXcpX50) of Example 1 which had constitutive promoters replaced for inducible promoters of araBAD operon, araFGH operon and araE, and for inducible promoters of xylAB operon and xylFGH operon and then was subjected to evolutionary adaptation in a xylose minimal medium (C), the strain (AXcpAX50) of Example 2 which had constitutive promoters replaced for inducible promoters of araBAD operon, araFGH operon and araE, and for inducible promoters of xylAB operon and xylFGH operon and then was subjected to evolutionary adaptation in an arabinose and xylose minimal medium (D), wherein residual concentrations of glucose and xylose are indicated by diamonds (♦) and rectangles (■), respectively.

As can be seen from FIGS. 7A to 7D, both the strain (AXcpX50) of Example 1 which had constitutive promoters replaced for inducible promoters of araBAD operon, araFGH operon and araE, and for inducible promoters of xylAB operon and xylFGH operon and then was subjected to evolutionary adaptation in a xylose minimal medium, and the strain (AXcpAX50) of Example 2 which had constitutive promoters replaced for inducible promoters of araBAD operon, araFGH operon and araE, and for inducible promoters of xylAB operon and xylFGH operon and then was subjected to evolutionary adaptation in an arabinose and xylose minimal medium were observed to simultaneously utilize glucose and xylose within 16 hrs whereas the wild-type E. coli essentially did not utilize xylose at all.

The results show that the constitutive expression of ara operon and xyl operon in combination with the evolutionary adaptation allows E. coli to mutate to simultaneously utilize glucose and xylose.

Test Example 3

Examination of Mutant E. coli for Molecular Mechanism for CCR Elimination

The mutant E. coli (AXcpAX50) of Example 1, capable of simultaneously utilizing glucose and xylose, was examined for CCR elimination based on new mutation, as follows.

Test strains were seeded in 50 mL of an M9-minimal supplemented with 2.5 g/L glucose and 2.5 g/L, xylose or with 5 g/L glucose and 5 g/L xylose, and cultured in the presence of 2 g/L CaCO$_3$. Thereafter, 1 mL of the culture medium was taken every three hours and measured for residual concentrations of glucose and xylose according to the method described in Test Example 2. All experiments were carried out in triplicate and data were expressed as a mean±standard deviation from three independent measurements.

Figure 8A:
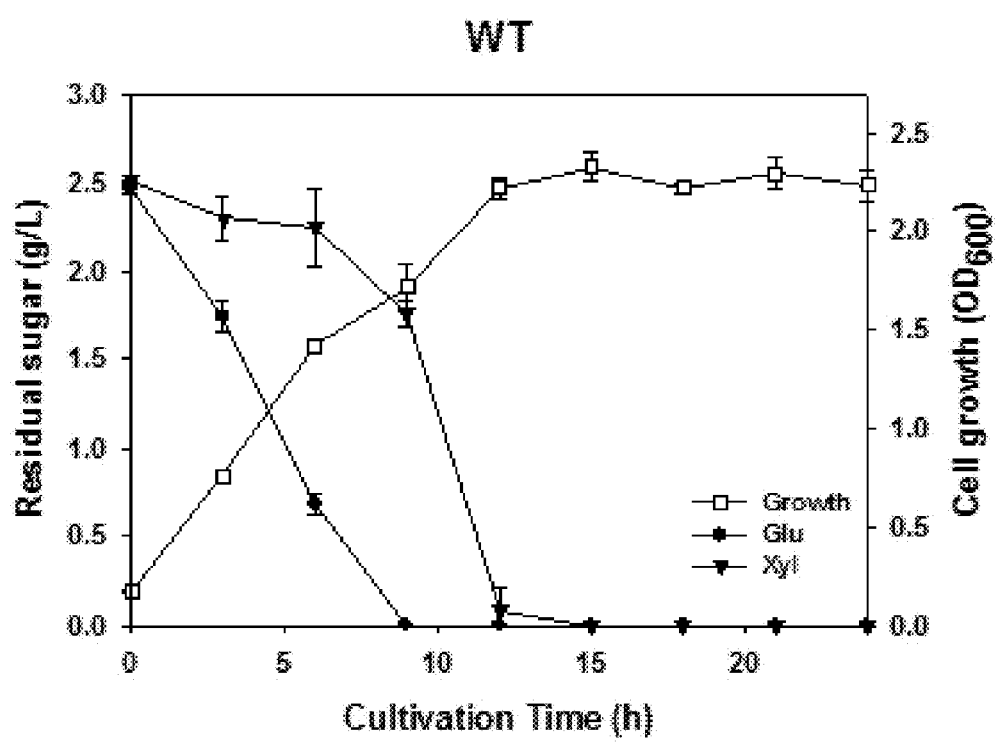
FIG. 8A depicts residual concentrations of glucose (●) and xylose (▼), and cell growth rates (□) of a wild-type *E. coli* MG1655 (WT)
Figure 8B:
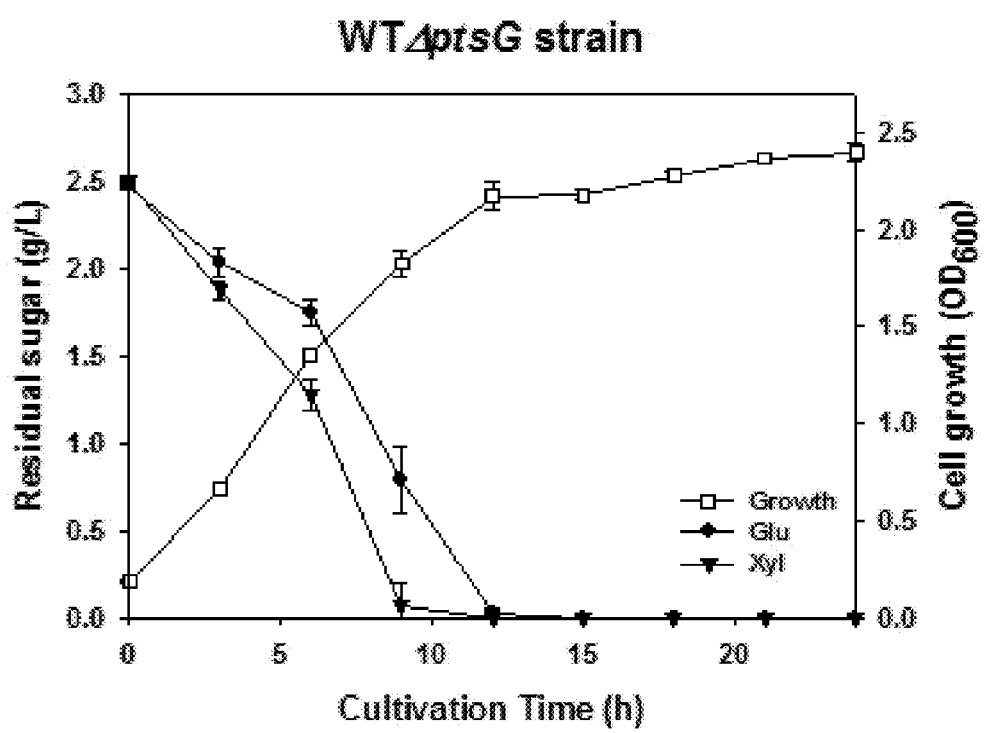
FIG. 8B depicts residual concentrations of glucose (●) and xylose (▼), and cell growth rates (□) of the ptsG-knockout wild-type strain (WTΔptsG) of Example <3-1>.
Figure 8C:
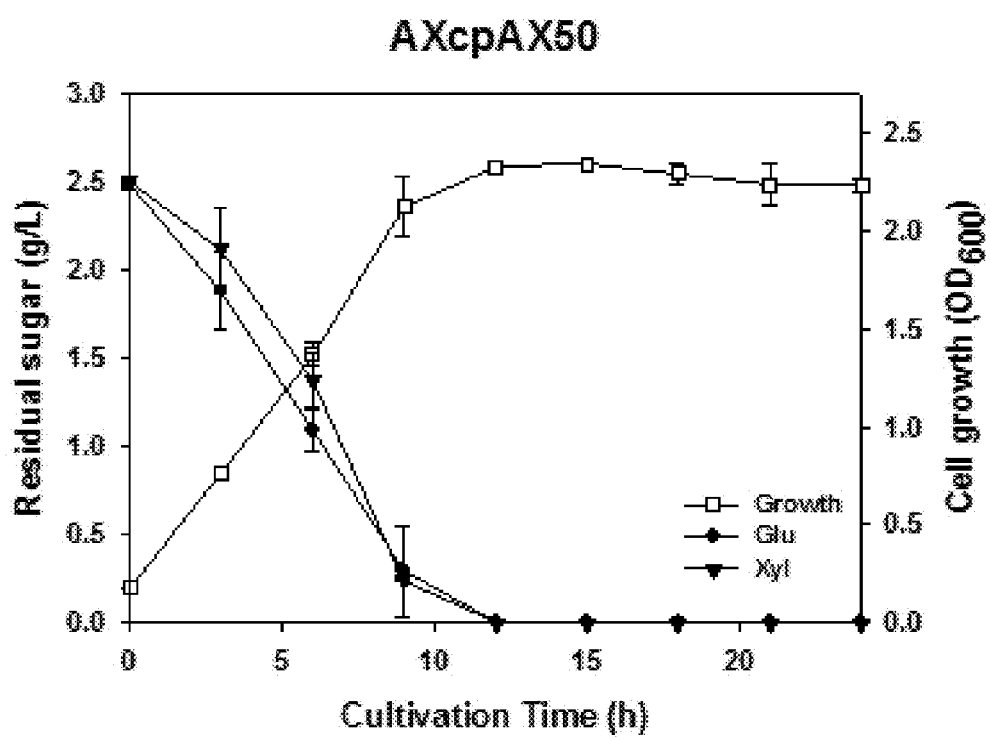
FIG. 8C depicts residual concentrations of glucose (●) and xylose (▼), and cell growth rates (□) of the mutant strain (AXcpAX50) of Example 2 (C)
Figure 8D:
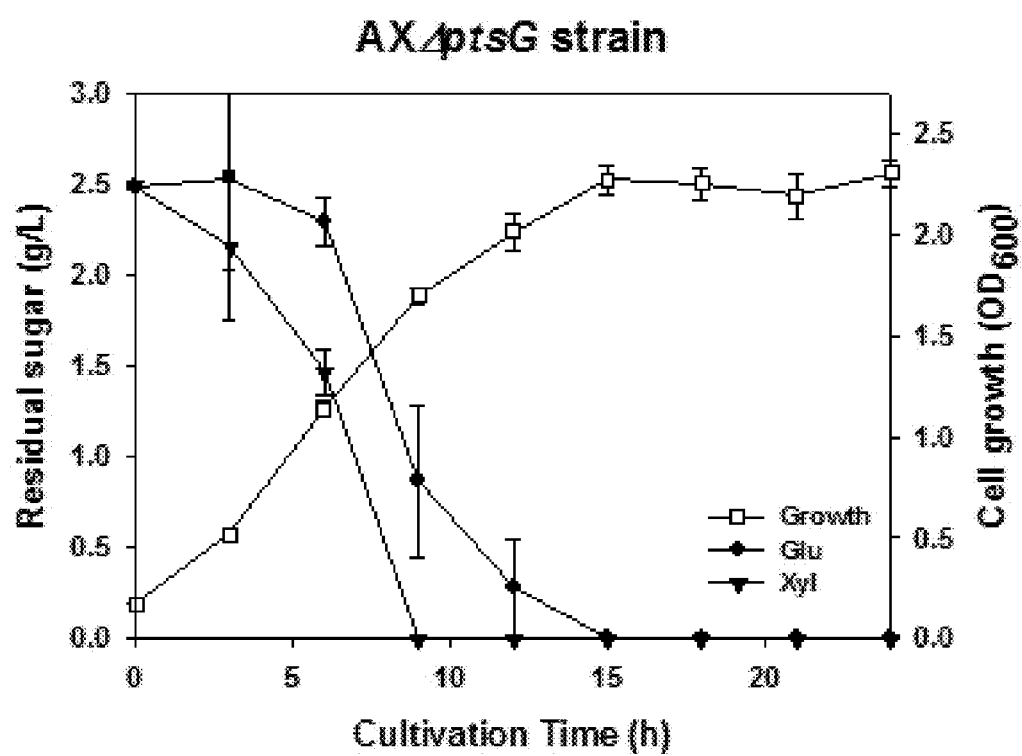
FIG. 8D depicts residual concentrations of glucose (●) and xylose (▼), and cell growth rates (□) of the ptsG-knockout AXcpAX50 strain (AXΔptsG) of Example <3-2>, wherein each of the strains are cultured in an M9-minimal medium containing glucose (2.5 g/L) and xylose (2.5 g/L).
Figure 9A:
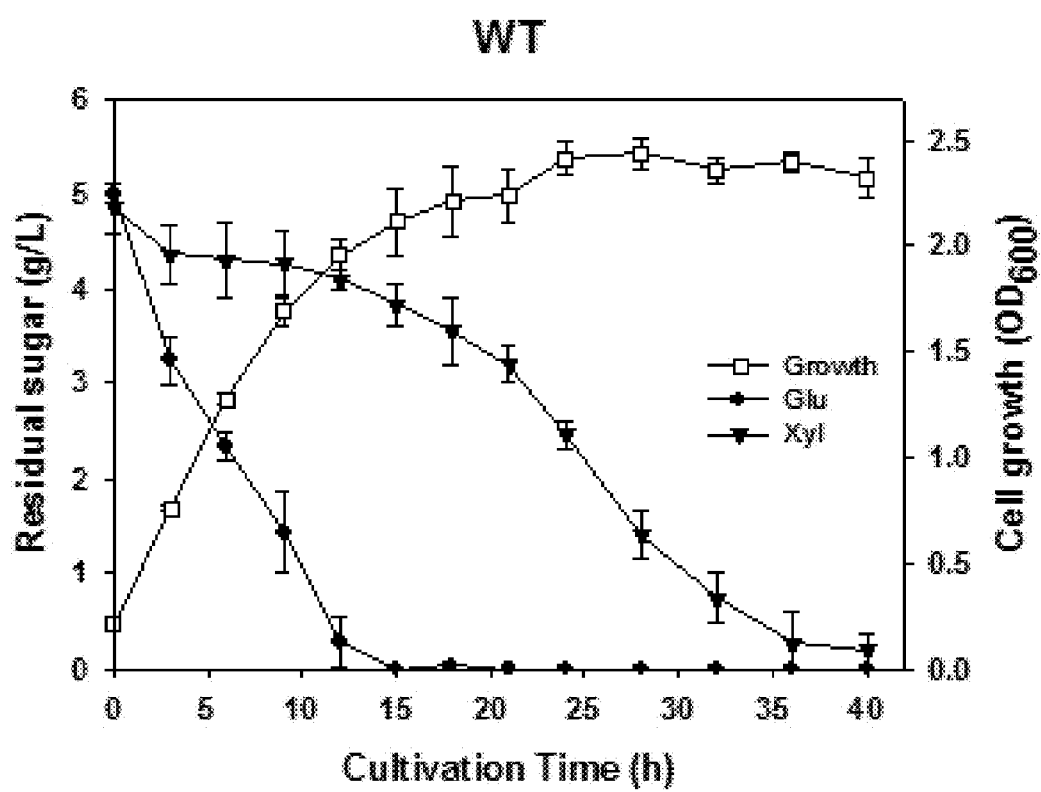
FIG. 9A depicts residual concentrations of glucose (●) and xylose (▼), and cell growth rates (□) of a wild-type *E. coli* MG1655 (WT)
Figure 9B:
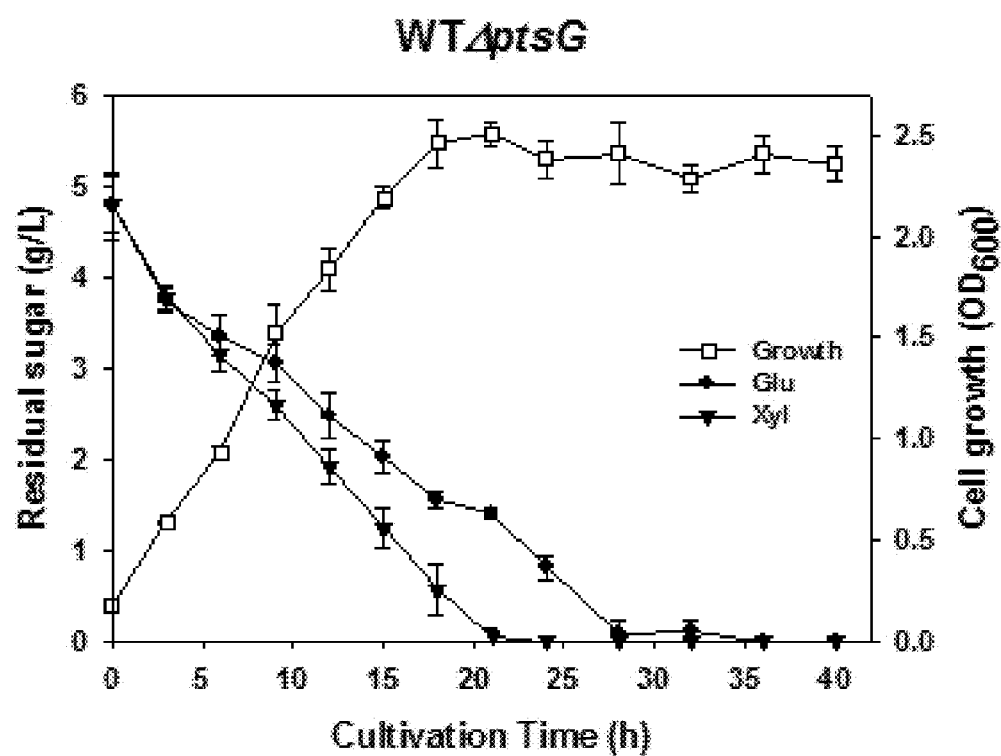
FIG. 9B depicts residual concentrations of glucose (●) and xylose (▼), and cell growth rates (□) of the ptsG-knockout wild-type strain (WTΔptsG) of Example <3-1>.
Figure 9C:
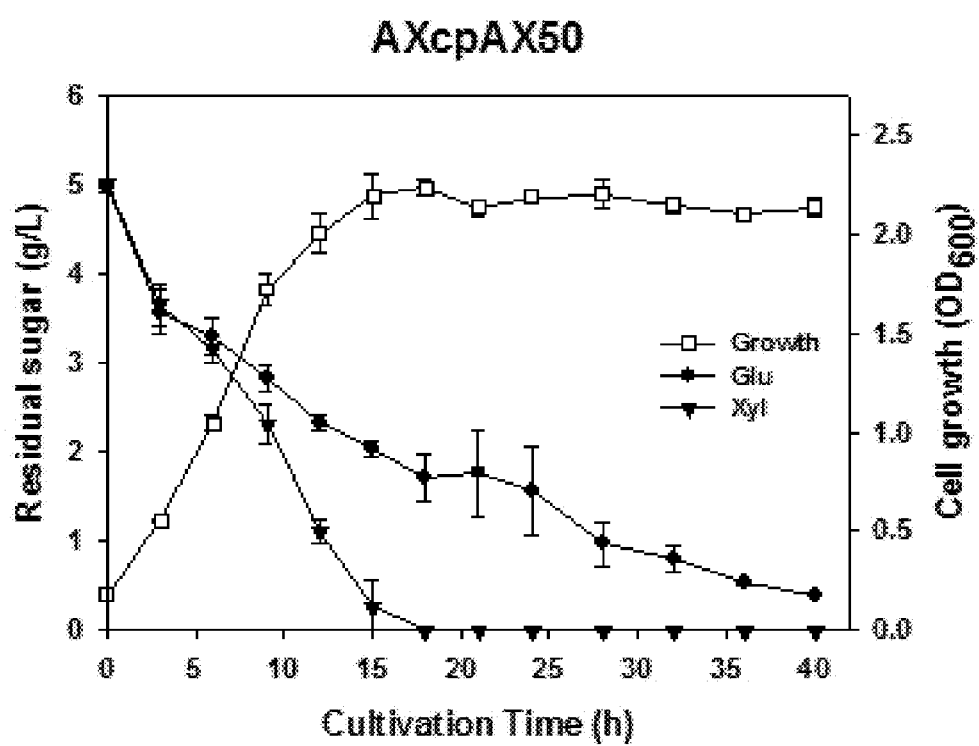
FIG. 9C depicts residual concentrations of glucose (●) and xylose (▼), and cell growth rates (□) of the mutant strain (AXcpAX50) of Example 2.
Figure 9D:
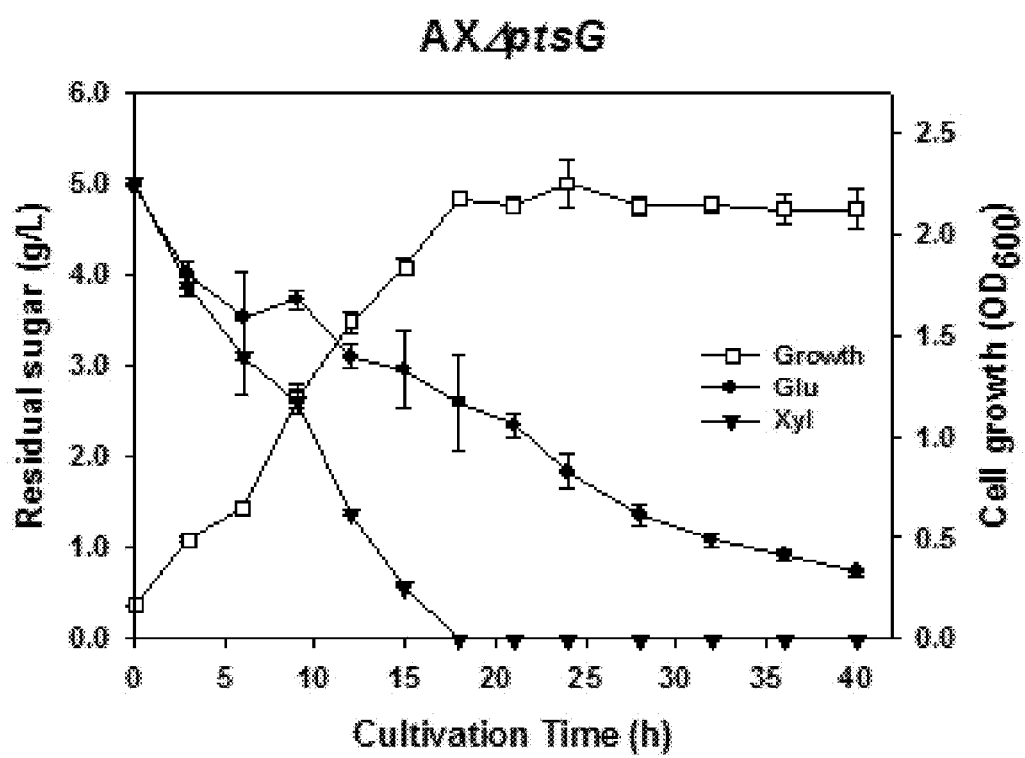
FIG. 9D depicts residual concentrations of glucose (●) and xylose (▼), and cell growth rates (□) of the ptsG-knockout AXcpAX50 strain (AXΔptsG) of Example <3-2>, when each of the above strains are cultured in an M9-minimal medium containing glucose (5.0 g/L) and xylose (5.0 g/L)

Test results are shown in FIGS. 8A to 8D for the M9-minimal medium supplemented with 2.5 g/L glucose and 2.5 g/L xylose, and in FIGS. 9A to 9D for the M9-minimal medium supplemented with 5 g/L glucose and 5 g/L xylose. FIGS. 8A and 9A are depicted with data from a wild-type *E. coli* MG1655 (WT), FIGS. 8B and 9B with data from ptsG-knockout wild-type strain (WTΔptsG) of Example <3-1>, FIGS. 8C and 9C with data from the mutant strain (AXcpAX50) of Example 2, and FIGS. 8D and 9D with data from ptsG-knockout AXcpAX50 strain (AXΔptsG) of Example <3-1>. In each figure, dark circles (●) trace residual concentrations of glucose, and inverted triangles (▼) indicate residual concentrations of xylose while white rectangles (□) are for growth rates of the cells.

As can be seen in FIGS. 8A to 8D, a wild-type *E. coli* MG1655 utilized xylose only after almost complete consumption of glucose, whereas both the ptsG-knockout wild-type strain (WTΔptsG) of Example <3-1> and the strain (AXcpAX50) of Example 2 simultaneously utilized glucose and xylose within 12 hrs. On the other hand, the ptsG-knockout strain (AXΔptsG) of Example <3-2> exhibited remarkably slow utilization of glucose only. These results indicate that the ptsG gene was expressed as the glucose transporter EIIBC$^{Glc}$ functioning normally in the mutant strain (AXcpAX50) of Example 2. Therefore, the simultaneous utilization of glucose and xylose by the mutant strain (AXcpAX50) of Example 2 is attributed to new genetic mutation other than the well-known ptsG disruption. Meanwhile, as is understood from data of FIGS. 9A to 9D, the mutant strain (AXcpAX50) of Example 2 grew with the active simultaneous metabolism of glucose and xylose even at a total concentration of 10 g/L of the sugars, and consumed sugars at a higher rate than did the wild-type.

Taken together, the results demonstrate that the mutant strain (AXcpAX50) capable of simultaneously utilizing glucose and xylose overcomes CCR thanks to the novel molecular mechanism other than the ptsG mutation.

Test Example 4

Genome Analysis of Mutant *E. coli*

Examination was made of sequences carrying mutations on the whole genomes of the AXcpX50 strain of Example 1 and the AXcpAX50 strain of Example 2. In this regard, DNA analysis was performed by NGS (next generation sequencing) to compare the strains of Examples 1 and 2 with a wild-type *E. coli* MG1655. Whole genes were analyzed in Macrogen Inc., Korea.

TABLE 7 summarizes mutations identified in the genomes of the mutant strains.

TABLE 7

| Mutant Strain | Relevant Region (Nomen-clature) | Mutant Sequence | Locus[a] | Effect on Protein[b] | Note |
|---|---|---|---|---|---|
| AXcpX50 | araF coding region (araF$_{\Delta11-15}$) | GGCTGCCA GACCAAT→ deleted | 1984108~ 1984122 | Disruption of signal sequence (11th~15th a.a.) | SEQ ID NO: 50 SEQ ID NO: 51 |
|  | araE coding region (araE$_{L126*}$) | T→(-) | 2979938 | Nonsense mutation (L126Stop) | SEQ ID NO: 52 SEQ ID NO: 53 |
|  | thiC upstream region (thiC$_{up}$) | C→A | 4194272 | Not determined | SEQ ID NO: 54 |
|  | xylA CP25 promoter (xylA$_{cp25}$) | G→T | 57th codon | Not determined | SEQ ID NO: 55 |
| AXcpAX50 | ybjG coding region (ybjG$_{D99G}$) | T→C | 882316 | Missense mutation (D99G) | SEQ ID NO: 56 SEQ ID NO: 57 |
|  | araE coding region (araE$_{S91I}$) | C→A | 2979933 | Missense mutation (S91I) | SEQ ID NO: 58 SEQ ID NO: 59 |
|  | pyrE upstream region (pyrE$_{up}$) | G→deleted | 3813833 | Not determined | SEQ ID NO: 60 |
|  | xylA CP25 promoter (xylA$_{cp25}$) | G→T | 57th codon | Not determined | SEQ ID NO: 55 |

[a]NCBI reference sequence NC_000913.2
[b]D: Aspartic acid, G: glycine, S: serine, I: isoleucine, L: leucine
*SEQ ID NOS: 51, 53, 57 and 59 represent the amino acid sequences translated by the nucleotide sequences of SEQ ID NOs: 50, 52, 56 and 58, respectively.

FIG. 10 compares nucleotide sequence alignments in modified DNA regions of individual strains while FIG. 11 shows peptide sequence alignments of the mutant genes.

The genome analysis identified that the mutant strains have seven mutant genes (araE$_{L126*}$, araE$_{S91I}$, araF$_{\Delta11-15}$, thiC$_{up}$, ybjG$_{D99G}$, pyrE$_{up}$, xylA$_{cp25}$) all of which have not yet been reported. Particularly, the four mutant genes (araE$_{S91I}$, ybjG$_{D99G}$, pyrE$_{up}$, xylA$_{cp25}$) detected in the mutant *E. coli* (AXcpAX50) of Example 2 are regarded as accounting for the phenotype of the simultaneous utilization of glucose and xylose, as demonstrated in Example 2.

These results obtained above indicate that the mutant strain capable of simultaneously utilizing glucose and xylose has a new genotype which has not been reported thus far.

Test Example 5

MAGE-Based Screening of Various *E. coli* Strains for Xylose Utilization

DNA sequences of modified genes of the mutant strains selected in Example 4 (AXcpM#1, AXcpM#4, AXcpM#9, AXcpM#14, AXcpM#15, AXcpM#22, AXcpM#24, AXcpM#26, AXcpM#28) were identified, and are summarized in Table 8, below.

TABLE 8

| Strain Origin | Gene | AXcpM | 1 | 4 | 9 | 14 | 15 | 22 | 24 | 26 | 28 |
|---|---|---|---|---|---|---|---|---|---|---|---|
| AXcpX50 | $araE_{L126*}$ | —[a] | — | — | — | — | — | — | — | — | — |
| | $araF_{\Delta11-15}$ | — | — | — | — | — | — | — | O[b] | — | — |
| | $thiC_{up}$ | — | — | — | — | — | — | — | — | — | — |
| AXcpAX50 | $araE_{S91I}$ | — | O | O | — | O | — | — | O | O | O |
| | $pyrE_{up}$ | — | — | — | — | — | — | — | — | — | — |
| | $ybjG_{D99G}$ | — | — | — | — | — | O | — | — | — | — |
| Both strain | $xylA_{cp25}$ | — | O | O | O | O | O | O | O | O | O |

[a] mutation not inserted;
[b] mutation inserted.

Figure 12:
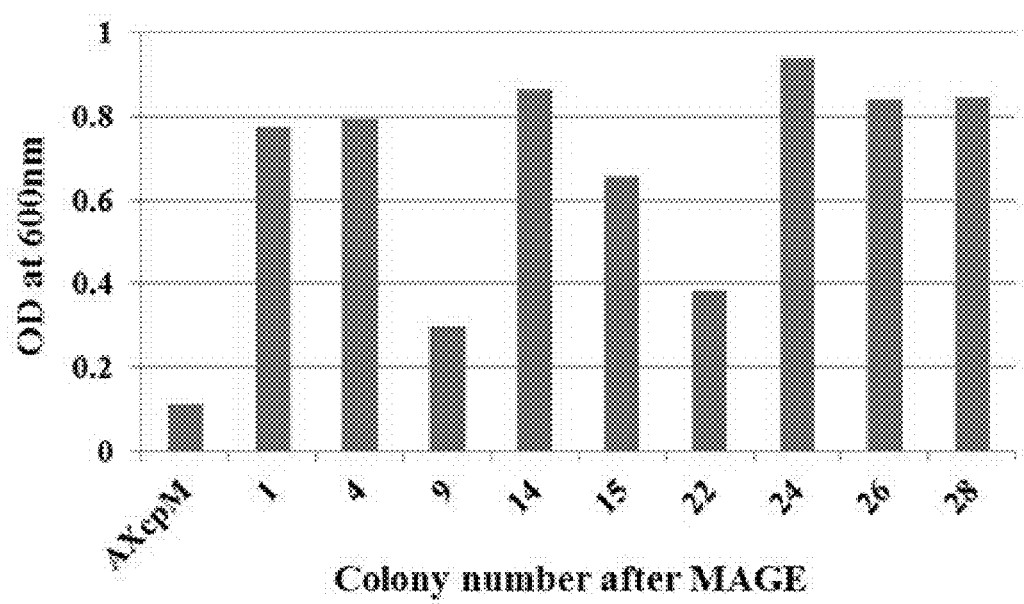
FIG. 12 is a graph of growth rates of various mutant strains selected in Example 4 according to xylose utilization after cultivation in a xylose minimal medium for 16 hrs.
Figure 13A:
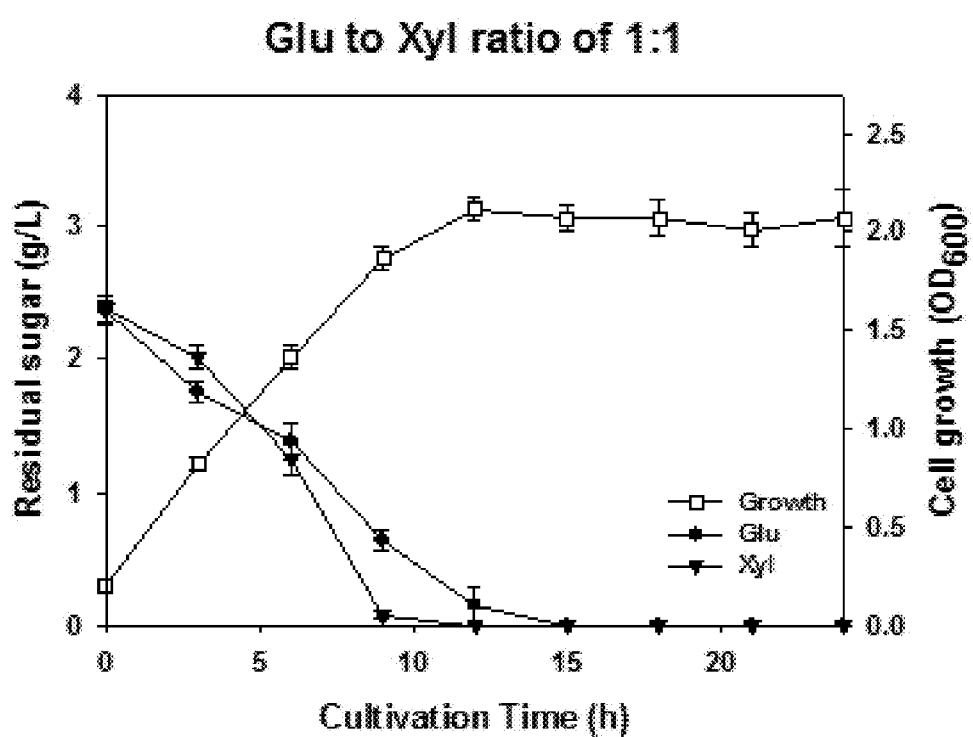
FIGS. 13A-13D depict residual concentrations of glucose (●) and xylose (▼), and growth rates (□) of the mutant strain (AXcpAX50) of Example 2 when the mutant strain is cultured in an M9-minimal medium containing glucose and xylose at a ratio of 1:1, 2:1, 3:1, or 4:1 (a total of 5 g/L), respectively.
Figure 13B:
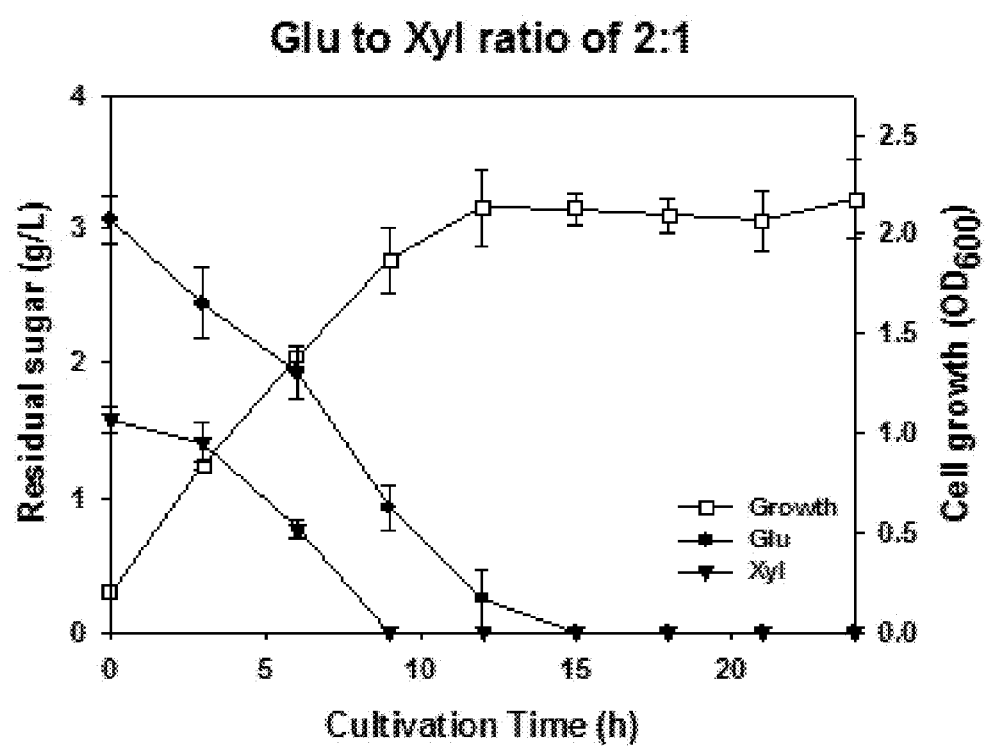
Figure 13C:
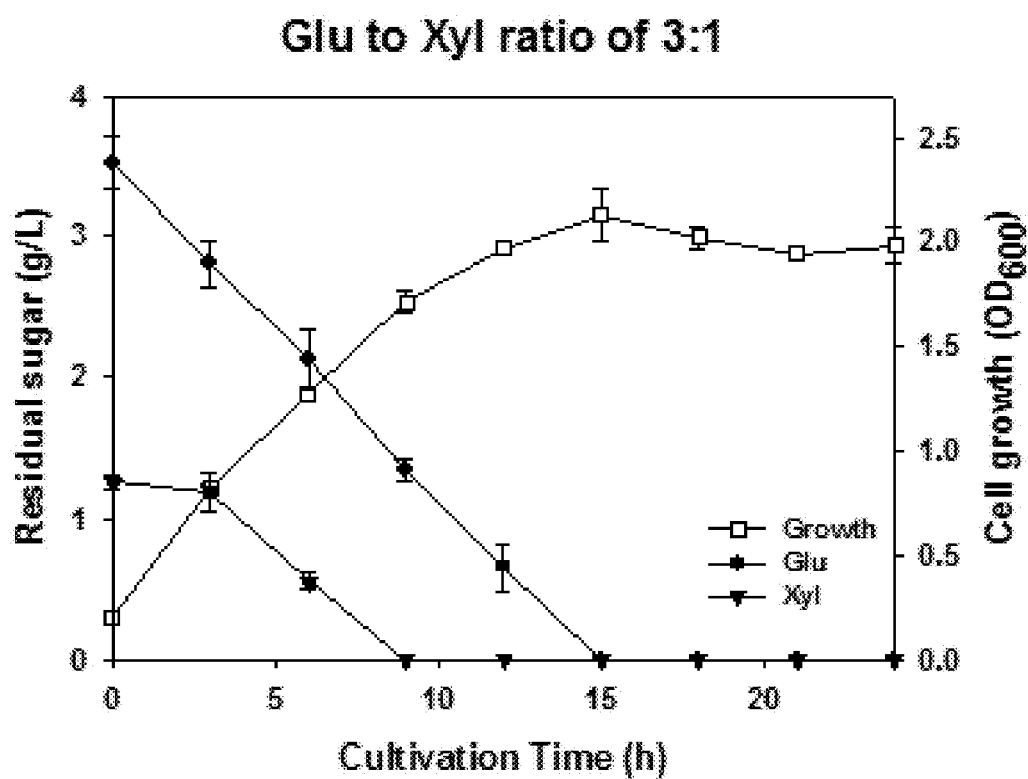
Figure 13D:
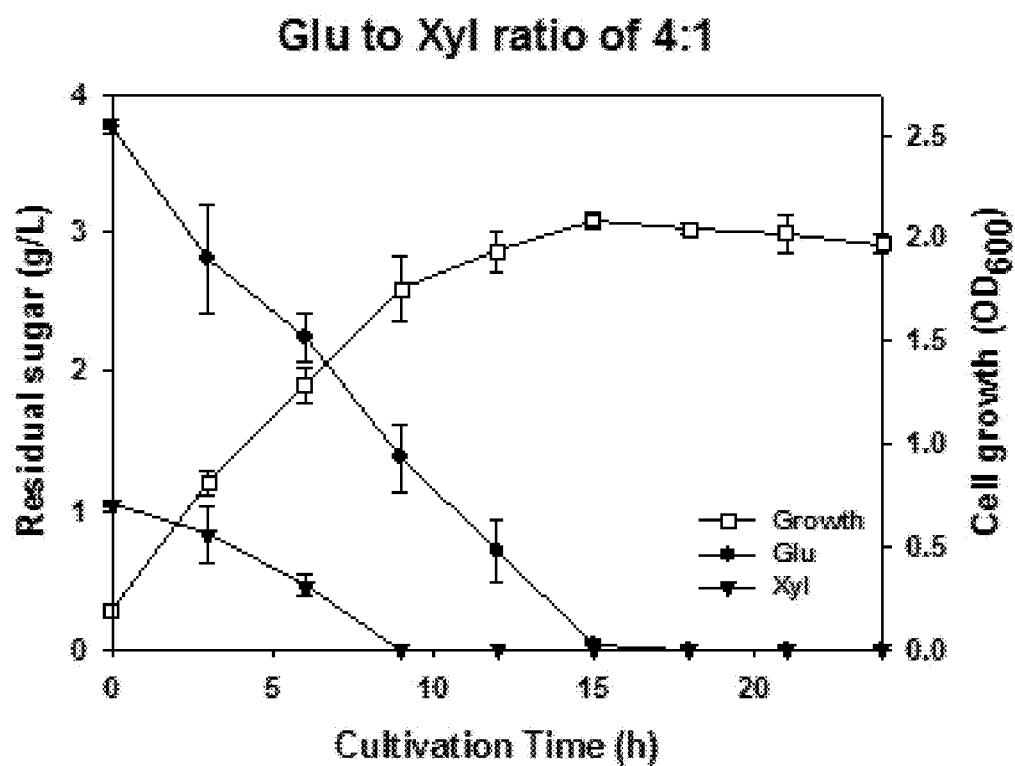

Meanwhile, after being cultured for 16 hrs in a xylose minimal medium, the various mutant strains selected in Example 4 were measured for growth rate according to xylose utilization. The results are given in FIG. 12.

AXcpM#9 and AXcpM#22 are strains which carry mutations only on the xylA CP25 promoter ($xylA_{cp25}$), and were found to grow 3- to 4-fold faster with xylose, compared to the control AXcpM. AXcpM#1, AXcpM#4, AXcpM#14, AXcpM#26, and AXcpM#28 in all of which $araE_{S91I}$, mutation of the 99th serine of the araE coding region to isoleucine, was detected together with the xylA CP25 promoter mutation ($xylA_{cp25}$) were observed to exhibit growth rates almost 8 times that of the control. AXcpM#24 in which $araF_{\Delta11-15}$, the deletion mutation of the signal sequence of araF, was detected, together with $xylA_{cp25}$ and $araE_{S91I}$, grew almost 9-fold faster. AXcpM#15, which has the mutations $xylA_{cp25}$ and $ybjG_{D99G}$ was observed to improve in growth rate by about 6 times, compared to the control.

The results obtained above indicate that the xylose pathway-related phenotype of various mutant strains is attributed to the newly discovered genotypes.

Test Example 6

Sugar Utilization Change with Glucose and Xylose Ratio of Mutant *E. coli* Strains The mutant *E. coli* (AXcpAX50) capable of simultaneously utilizing glucose and xylose of Example 2 was examined for sugar utilization at various sugar ratios as follows.

The mutant strain (AXcpAX50) of Example 2 was seeded in 50 mL of an M9-minimal medium containing glucose and xylose at a ratio of 1:1, 2:1, 3:1, or 4:1 (total 5 g/L), and cultured in the presence of 2 g/L $CaCO_3$. Every three hours during cultivation, 1 mL of the culture medium was withdrawn, and measured for residual concentrations of glucose and xylose. All experiments were carried out in triplicate and data were expressed as a mean±standard deviation from three independent measurements.

Test results are shown in FIGS. 13A to 13D for the media containing glucose and xylose at a ratio of 1:1, 2:1, 3:1, and 4:1 where dark circles (●) trace residual concentrations of glucose, and inverted triangles (▼) indicate residual concentrations of xylose while white rectangles (□) show optical densities accounting for growth rates of the cells.

As can be seen in FIGS. 13A to 13D, the AXcpAX50 strain of Example 2 exhibited simultaneous utilization of glucose and xylose at all the ratios of the sugars. When account is taken of the practical situation that sugar mixtures in biomass hydrolysates contain various glucose-xylose ratios, the mutant strain (AXcpAX50) of the present invention is expected to exhibit simultaneous utilization of glucose and xylose even at a broad range of glucose-xylose ratios.

Taken together, the results obtained above demonstrate that the mutant strain (AXcpAX50) capable of simultaneously utilizing glucose and xylose works effectively even at various ratios of sugars.

Test Example 7

Xylitol Production by Mutant *E. coli*

The xylitol-producing strains established in Example 5 were assayed for xylitol productivity.

Briefly, each test strain was cultured in 70 mL of an M9-minimal medium supplemented with 5.8 g/L glucose and 4.2 g/L xylose in a customized bioreactor designed to keep a pH of 7 with 3 M sodium hydroxide (NaOH). At the time point of 6 hrs after culturing, 0.1 mM IPTG was added to induce the expression of xylose reductase. At time points of 6 hrs and 13 hrs after culturing, a mixture of 5.8 g/L glucose and 4.2 g/L xylose was further added to the cell culture. After being taken from the bioreactor, 1 mL of the cell culture was measured for xylitol concentration in the same manner as in Example 2.

Figure 14A:
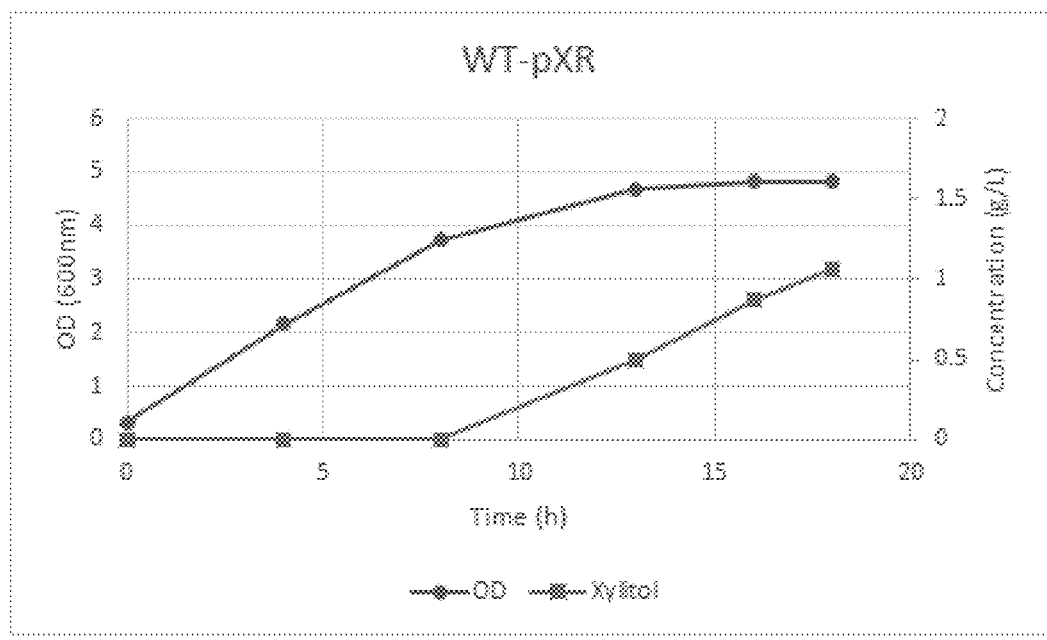
FIGS. 14A and 14B depict xylitol production (■), and growth rates (●) of the WT-pXR strain (A), respectively, and the AX-pXR strain (B), obtained in Example 5, when the strains are cultured in an M9-minimal medium containing 5.8 g/L glucose and 4.2 g/L xylose.
Figure 14B:
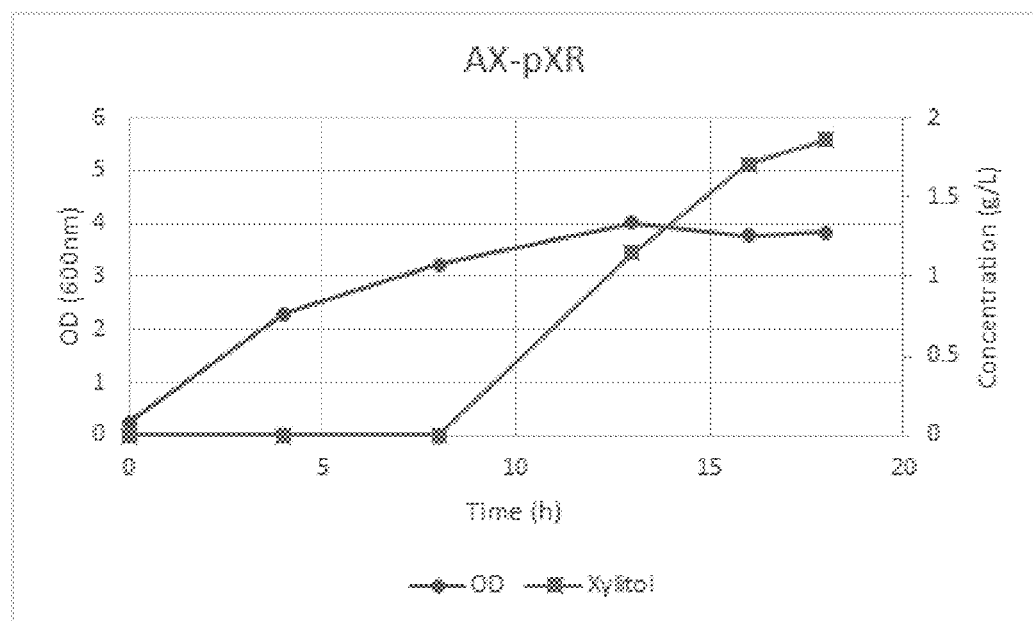

Test results are shown in FIGS. 14A and 14B for the WT-pXR strain of Example 5, derived from *E. coli* MG1655, and the Ax-PXR strain of Example 5, derived from the mutant strain (AXcpAX50), respectively. In each figure, dark rectangles (■) trace xylitol production while dark circles (●) indicate optical densities accounting for growth rates of the strains. As can be seen in FIGS. 14A and 14B, AX-pXR produced xylitol at an about two-fold greater rate than did WT-pXR.

These data obtained above indicate that the AX-pXR strain derived from AXcpAX50 capable of simultaneously utilizing glucose and xylose is more effective in producing valuable chemicals from a biomass than id the WT-pXR strain derived from a wild-type *E. coli* which utilizes xylose after the consumption of glucose.

While the invention has been described with respect to the above specific embodiments, it should be recognized that various modifications and changes may be made to the invention by those skilled in the art which also fall within the scope of the invention as defined by the appended claims.

What is claimed is:

1. A method for preparing a mutant *E. coli* capable of simultaneously utilizing glucose and xylose from a wild-type *E. coli*, comprising:
   (1) replacing inducible promoters of araBAD operon, araFGH operon, araE gene, xylAB operon, and xylFGH operon of the wild-type *E. coli* with respective constitutive promoters; and
   (2) growing the promoter-replaced *E. coli* in a xylose minimal medium or an arabinose and xylose minimal medium for 10 days or longer.

2. The method of claim 1, wherein the inducible promoters of araBAD operon, araFGH operon, araE gene, xylAB operon, and xylFGH operon have nucleotide sequences of SEQ ID NOS: 1 to 5, respectively.

3. The method of claim 1, wherein the constitutive promoters have the nucleotide sequence of SEQ ID NO: 6 or 7.

4. The method of claim 1, wherein the xylose minimal medium is an M9-minimal medium containing xylose 4 g/L, disodium hydrogen phosphate 6.78 g/L, potassium phosphate monobasic 3.0 g/L, sodium chloride 0.5 g/L, ammonium chloride 1.0 g/L, magnesium sulfate 2 mM, and calcium chloride 0.1 mM.

5. The method of claim 1, wherein the arabinose and xylose minimal medium is an M9-minimal medium containing arabinose 2 g/L, xylose 2 g/L, disodium hydrogen phosphate 6.78 g/L, potassium phosphate monobasic 3.0 g/L, sodium chloride 0.5 g/L, ammonium chloride 1.0 g/L, magnesium sulfate 2 mM, and calcium chloride 0.1 mM.

6. A mutant *E. coli*, capable of simultaneously utilizing glucose and xylose, prepared by replacing inducible promoters of araBAD operon, araFGH operon, araE gene, xylAB operon, and xylFGH operon of wild-type *E. coli* with respective constitutive promoters, and growing the promoter-replaced *E. coli* in a xylose minimal medium or an arabinose and xylose minimal medium for 10 days or longer.

7. The mutant *E. coli* of claim 6, wherein the inducible promoters of araBAD operon, araFGH operon, araE gene, xylAB operon and xylFGH operon have nucleotide sequences of SEQ ID NOS: 1 to 5, respectively.

8. The mutant *E. coli* of claim 6, wherein the constitutive promoters have the nucleotide sequence of SEQ ID NO: 6 or 7.

9. The mutant *E. coli* of claim 6, which comprises mutations represented by the nucleotide sequences of SEQ ID NOS: 55, 56, 58, and 60.

10. The mutant *E. coli* of claim 6, which comprises mutations represented by the amino acid sequences of SEQ ID NOS: 51 and 53.

11. The mutant *E. coli* of claim 6, which comprises mutations represented by the nucleotide sequences of SEQ ID NOS: 50, 52, 54, and 55.

12. The mutant *E. coli* of claim 6, which comprises mutations represented by the amino acid sequences of SEQ ID NOS: 57 and 59.

13. A method for producing a biofuel, a biologically active ingredient, a medicinal material, or a chemical substance for the chemical industry from a biomass by using a mutant *E. coli* capable of simultaneously utilizing glucose and xylose, said mutant *E. coli* being prepared by replacing inducible promoters of araBAD operon, araFGH operon, araE gene, xylAB operon, and xylFGH operon of a wild-type *E. coli* with respective constitutive promoters, and growing the promoter-replaced *E. coli* in a xylose minimal medium or an arabinose and xylose minimal medium for 10 days or longer.

\* \* \* \* \*